US011236147B2

(12) United States Patent
Ingber et al.

(10) Patent No.: US 11,236,147 B2
(45) Date of Patent: Feb. 1, 2022

(54) METHODS AND COMPOSITIONS FOR THE INHIBITION OF TRPV4

(71) Applicant: CHILDREN'S MEDICAL CENTER CORPORATION, Boston, MA (US)

(72) Inventors: Donald E. Ingber, Boston, MA (US); Mariko Kobayashi, Brookline, MA (US)

(73) Assignee: CHILDREN'S MEDICAL CENTER CORPORATION, Boston, MA (US)

(*) Notice: Subject to any disclaimer, the term of this patent is extended or adjusted under 35 U.S.C. 154(b) by 496 days.

(21) Appl. No.: 16/034,894

(22) Filed: Jul. 13, 2018

(65) Prior Publication Data

US 2019/0002527 A1    Jan. 3, 2019

Related U.S. Application Data

(63) Continuation of application No. 14/900,265, filed as application No. PCT/US2014/043785 on Jun. 24, 2014, now Pat. No. 10,047,140.

(60) Provisional application No. 61/838,488, filed on Jun. 24, 2013.

(51) Int. Cl.
*C07K 14/705* (2006.01)
*A61K 38/00* (2006.01)

(52) U.S. Cl.
CPC ...... *C07K 14/70596* (2013.01); *C07K 14/705* (2013.01); *A61K 38/00* (2013.01); *C07K 2319/10* (2013.01)

(58) Field of Classification Search
CPC . C07K 14/70596; C07K 14/705; A61K 38/00
See application file for complete search history.

(56) References Cited

U.S. PATENT DOCUMENTS

| | | | |
|---|---|---|---|
| 2003/0185862 | A1 | 10/2003 | Kang et al. |
| 2010/0061977 | A1 | 3/2010 | Ruben et al. |

OTHER PUBLICATIONS

Ginn et al. Gene therapy clinical trials worldwide to 2012—an update. The Journal of Gene Medicine, vol. 15, pp. 65-77, 2013. (Year: 2012).*
Multiple Alignment for HomoloGene: 11003, https://www.ncbi.nlm.nih.gov/homologene/?term=trpv4&report=multiplealignment, printed as pp. 1/9-9/9 on Feb. 11, 2021. (Year: 2021).*
Nilius et al. The puzzle of TRPV4 channelopathies. EMBO Reports, vol. 14, No. 2, pp. 152-163, Jan. 11, 2013. (Year: 2013).*
Bartus, R.T. Translating the therapeutic potential of neurotrophic factors to clinical 'proof of concept': A personal saga achieving a career-long quest. Neurobiology of Disease, vol. 48, pp. 153-178, 2012. (Year: 2012).*
GenBank Accession No. J02769.1, publicly available Oct. 1994, printed as pp. 1/2-2/2. (Year: 1994).*
GenBank Accession No. AAA51540.1, publicly available Oct. 1994, printed as pp. 1/2-2/2. (Year: 1994).*
Bröer et al., "Association of 4F2hc with light chains LAT1, LAT2 or y+ LAT2 requires different domains." Biochemical Journal 355(3):725-731 (2001).
Chira et al., "Progresses towards safe and efficient gene therapy vectors." Oncotarget 6(31):30675-30703 (2015).
Edelstein et al., "Gene therapy clinical trials worldwide 1989-2004—an overview." The Journal of Gene Medicine 6(6):597-602 (2004).
Everett et al., "Pendred syndrome is caused by mutations in a putative sulphate transporter gene (PDS)." Nature Genetics 17(4):411-422 (1997).
Feral et al., "CD98hc (SLC3A2) participates in fibronectin matrix assembly by mediating integrin signaling", The Journal of Cell Biology, 178(4):701-711 (2007).
Hara et al., "Enhanced tumorigenicity caused by truncation of the extracellular domain of GP125/CD98 heavy chain." Oncogene 19(54):6209-6215 (2000).
Kolesnikova et al., "Beta1 integrins show specific association with CD98 protein in low density membranes" BMC Biochemistry, 2:10 (2001).
Luo et al., "Synthetic DNA delivery systems." Nature Biotechnology 18(1):33-37 (2000).
Matthews et al, "Ultra-rapid activation of TRPV4 ion channels by mechanical forces applied to cell surface b1 integrins", Integr Biol., 2(9):435-442 (2010).
Palu et al., "In pursuit of new developments for gene therapy of human diseases." Journal of Biotechnology 68(1):1-13 (1999).
Scott et al., "The Pendred syndrome gene encodes a chloride-iodide transport protein." Nature Genetics 21(4):440-443 (1999).
Teixeira et al., "Primary structure of the human 4F2 antigen heavy chain predicts a transmembrane protein with a cytoplasmic NH2 terminus." Journal of Biological Chemistry 262(20):9574-9580 (1987).
Thodeit et al., "TRPV4 channels mediate cyclic strain-induced endothelial cell reorientation through integrin to integrin signaling", Circ Res., 104(9):1123-1130 (2009).
Thorneloe et al., "An Orally Active TRPV4 Channel Blocker Prevents and Resolves Pulmonary Edema Induced by Heart Failure", Science Translation Medicine, 4(159):159ra148 (2012).
Verma et al., "Gene therapy: twenty-first century medicine." Annu. Rev. Biochem. 74:711-738 (2005).
Verma et al., "Gene therapy—promises, problems and prospects." Nature 389(6648):239-242 (1997).
Wang et al., "Rapid and highly efficient transduction by double-stranded adeno-associated virus vectors in vitro and in vivo." Gene Therapy 10(26):2105-2111 (2003).
Everaerts et al. "The vanilloid transient receptor potential channel TRPV4: from structure to disease." Progress in Biophysics and Molecular Biology 103(1): 2-17 (2010).
Ferrer-Montiel et al. "Advances in modulating thermosensory TRP channels." Expert Opinion on Therapeutic Patents 22(9): 999-1017 (2012).

(Continued)

*Primary Examiner* — Jennifer Dunston
(74) *Attorney, Agent, or Firm* — Nixon Peabody LLP; David S. Resnick; Nicole D. Kling

(57) ABSTRACT

TRPV4 activation increases vascular permeability and can be triggered by both chemical and mechanical cues. This activation of TRPV4 can contribute to a number of pathological conditions, e.g., edema, inflammation, hypertension, and/or hyperalgesia. Described herein are methods and compositions relating to inhibition of mechanically-induced TRPV4 activation, e.g., for the treatment of pulmonary edema, edema, inflammation, hypertension, and/or hyperalgesia.

8 Claims, 12 Drawing Sheets

Specification includes a Sequence Listing.

(56) References Cited

OTHER PUBLICATIONS

Jia et al. "Functional TRPV4 channels are expressed in human airway smooth muscle cells." American Journal of Physiology—Lung Cellular and Molecular Physiology 287(2): L272-L278 (2004).
Kang. "The mutation of transient receptor potential vanilloid 4 (TRPV4) cation channel in human diseases." In Mutagenesis, ed. R. Mishra: Chapter 7, pp. 141-152 (2012).
Rock et al. "Gain-of-function mutations in TRPV4 cause autosomal dominant brachyolmia." Nature Genetics 40(8): 999-1003 (2008).
Todaka et al. "Warm temperature-sensitive transient receptor potential vanilloid 4 (TRPV4) plays an essential role in thermal hyperalgesia." Journal of Biological Chemistry 279(34): 35133-35138 (2004).
Zhu et al. "Association of TRPV4 gene polymorphisms with chronic obstructive pulmonary disease." Human Molecular Benetics 18(11): 2053-2062 (2009).

\* cited by examiner

```
                 160                                           210aa
HUMAN CD98       KFTGLSKEELLKVAGSPGWVRTRWALLLLFWLGWLGMLAGAVVIIVRAPRC
MOUSE CD98       KFTGLSKEELLKVAGSPGWVRTRWALLLLFWLGWLGMLAGAVVIIVRAPRC
XENOPUS CD98     KFTGLSKEELLRVAGTPTWVRVRWALLILFWLGWAGMLAGAVVIIVQAPRC
DROSOPHILA CD98  AFTGMSKEELMKYANDPFWVRLRWIFFVCFWAIWVGMLVGAILIIIGAPKC
                 ***:******:: *. * *** ** ::: **   * ***.**:**: **:*
```

FIG. 9

SEQUENCE LISTING

<160> NUMBER OF SEQ ID NOS: 26

<210> SEQ ID NO 1
<211> LENGTH: 51
<212> TYPE: PRT

```
<213> ORGANISM: Unknown
<220> FEATURE:
<223> OTHER INFORMATION: Description of Unknown: CD98 high homology
      domain sequence

<400> SEQUENCE: 1

Lys Phe Thr Gly Leu Ser Lys Glu Glu Leu Leu Lys Val Ala Gly Ser
1               5                   10                  15

Pro Gly Trp Val Arg Thr Arg Trp Ala Leu Leu Leu Leu Phe Trp Leu
            20                  25                  30

Gly Trp Leu Gly Met Leu Ala Gly Ala Val Val Ile Ile Val Arg Ala
        35                  40                  45

Pro Arg Cys
    50

<210> SEQ ID NO 2
<211> LENGTH: 3250
<212> TYPE: DNA
<213> ORGANISM: Homo sapiens

<400> SEQUENCE: 2
```

| | | | | | |
|---|---|---|---|---|---|
| ccggccggga | ttcaggaagc | gcggatctcc | cggccgccgg | cgcccagccg | tcccggaggc | 60 |
| tgagcagtgc | agacgggcct | ggggcaggca | tggcggattc | cagcgaaggc | ccccgcgcgg | 120 |
| ggcccgggga | ggtggctgag | ctccccgggg | atgagagtgg | cacccaggt | ggggaggctt | 180 |
| ttcctctctc | ctccctggcc | aatctgtttg | aggggagga | tggctccctt | tcgccctcac | 240 |
| cggctgatgc | cagtcgccct | gctggcccag | gcgatgggcg | accaaatctg | cgcatgaagt | 300 |
| tccagggcgc | cttccgcaag | ggggtgccca | accccatcga | tctgctggag | tccaccctat | 360 |
| atgagtcctc | ggtggtgcct | gggcccaaga | aagcacccat | ggactcactg | tttgactacg | 420 |
| gcacctatcg | tcaccactcc | agtgacaaca | agaggtggag | gaagaagatc | atagagaagc | 480 |
| agccgcagag | ccccaaagcc | cctgccctc | agccgccccc | catcctcaaa | gtcttcaacc | 540 |
| ggcctatcct | ctttgacatc | gtgtcccggg | gctccactgc | tgacctggac | gggctgctcc | 600 |
| cattcttgct | gacccacaag | aaacgcctaa | ctgatgagga | gtttcgagag | ccatctacgg | 660 |
| ggaagacctg | cctgcccaag | gccttgctga | acctgagcaa | tggccgcaac | gacaccatcc | 720 |
| ctgtgctgct | ggacatcgcg | gagcgcaccg | gcaacatgag | ggagttcatt | aactcgccct | 780 |
| tccgtgacat | ctactatcga | ggtcagacag | ccctgcacat | cgccattgag | cgtcgctgca | 840 |
| aacactacgt | ggaacttctc | gtggcccagg | gagctgatgt | ccacgcccag | gcccgtgggc | 900 |
| gcttcttcca | gccaaggat | gaggggggct | acttctactt | tggggagctg | cccctgtcgc | 960 |
| tggctgcctg | caccaaccag | ccccacattg | tcaactacct | gacggagaac | ccccacaaga | 1020 |
| aggcggacat | cgcgcgccag | gactcgcgag | caaacacagt | gctgcatgcg | ctggtggcca | 1080 |
| ttgctgacaa | cacccgtgag | aacaccaagt | ttgttaccaa | gatgtacgac | ctgctgctgc | 1140 |
| tcaagtgtgc | ccgcctcttc | cccgacagca | acctggaggc | cgtgctcaac | aacgacggcc | 1200 |
| tctcgccct | catgatggct | gccaagacgg | gcaagattgg | gatctttcag | cacatcatcc | 1260 |
| ggcgggaggt | gacggatgag | gacacacggc | acctgtcccg | caagttcaag | gactgggcct | 1320 |
| atgggccagt | gtattcctcg | ctttatgacc | tctcctccct | ggacacgtgt | ggggaagagg | 1380 |
| cctccgtgct | ggagatcctg | gtgtacaaca | gcaagattga | aaccgccac | gagatgctgg | 1440 |
| ctgtggagcc | catcaatgaa | ctgctgcggg | acaagtggcg | caagttcggg | gccgtctcct | 1500 |
| tctacatcaa | cgtggtctcc | tacctgtgtg | ccatggtcat | cttcactctc | accgcctact | 1560 |

-continued

| | |
|---|---|
| accagccgct ggagggcaca ccgccgtacc cttaccgcac cacggtggac tacctgcggc | 1620 |
| tggctggcga ggtcattacg ctcttcactg gggtcctgtt cttcttcacc aacatcaaag | 1680 |
| acttgttcat gaagaaatgc cctggagtga attctctctt cattgatggc tccttccagc | 1740 |
| tgctctactt catctactct gtcctggtga tcgtctcagc agccctctac ctggcaggga | 1800 |
| tcgaggccta cctggccgtg atggtctttg ccctggtcct gggctggatg aatgcccttt | 1860 |
| acttcacccg tgggctgaag ctgacgggga cctatagcat catgatccag aagattctct | 1920 |
| tcaaggacct tttccgattc ctgctcgtct acttgctctt catgatcggc tacgcttcag | 1980 |
| ccctggtctc cctcctgaac ccgtgtgcca acatgaaggt gtgcaatgag gaccagacca | 2040 |
| actgcacagt gcccacttac ccctcgtgcc gtgacagcga gaccttcagc accttcctcc | 2100 |
| tggacctgtt taagctgacc atcggcatgg gcgacctgga gatgctgagc agcaccaagt | 2160 |
| accccgtggt cttcatcatc ctgctggtga cctacatcat cctcaccttt gtgctgctcc | 2220 |
| tcaacatgct cattgccctc atgggcgaga cagtgggcca ggtctccaag gagagcaagc | 2280 |
| acatctggaa gctgcagtgg gccaccacca tcctggacat tgagcgctcc ttccccgtat | 2340 |
| tcctgaggaa ggccttccgc tctggggaga tggtcaccgt gggcaagagc tcggacggca | 2400 |
| ctcctgaccg caggtggtgc ttcagggtgg atgaggtgaa ctggtctcac tggaaccaga | 2460 |
| acttgggcat catcaacgag acccggggca agaatgagac ctaccagtat tatggcttct | 2520 |
| cgcataccgt gggccgcctc cgcagggatc gctggtcctc ggtggtaccc cgcgtggtgg | 2580 |
| aactgaacaa gaactcgaac ccggacgagg tggtggtgcc tctggacagc atggggaacc | 2640 |
| cccgctgcga tggccaccag cagggttacc cccgcaagtg gaggactgat gacgccccgc | 2700 |
| tctagggact gcagcccagc ccagcttct ctgcccactc atttctagtc cagccgcatt | 2760 |
| tcagcagtgc cttctggggt gtcccccac accctgcttt ggcccagag gcgagggacc | 2820 |
| agtggaggtg ccagggaggc cccaggaccc tgtggtcccc tggctctgcc tccccaccct | 2880 |
| ggggtgggg ctcccggcca cctgtcttgc tcctatggag tcacataagc caacgccaga | 2940 |
| gcccctccac ctcaggcccc agcccctgcc tctccattat ttatttgctc tgctctcagg | 3000 |
| aagcgacgtg accgctgccc cagctggaac ctggcagagg ccttaggacc ccgttccaag | 3060 |
| tgcactgccc ggccaagccc cagcctcagc ctgcgcctga gctgcatgcg ccaccatttt | 3120 |
| tggcagcgtg gcagctttgc aaggggctgg ggccctcggc gtggggccat gccttctgtg | 3180 |
| tgttctgtag tgtctgggat ttgccggtgc tcaataaatg tttattcatt gacggtggaa | 3240 |
| aaaaaaaaaa | 3250 |

<210> SEQ ID NO 3
<211> LENGTH: 871
<212> TYPE: PRT
<213> ORGANISM: Homo sapiens

<400> SEQUENCE: 3

Met Ala Asp Ser Ser Glu Gly Pro Arg Ala Gly Pro Gly Glu Val Ala
1               5                   10                  15

Glu Leu Pro Gly Asp Glu Ser Gly Thr Pro Gly Gly Glu Ala Phe Pro
            20                  25                  30

Leu Ser Ser Leu Ala Asn Leu Phe Glu Gly Glu Asp Gly Ser Leu Ser
        35                  40                  45

Pro Ser Pro Ala Asp Ala Ser Arg Pro Ala Gly Pro Gly Asp Gly Arg
    50                  55                  60

Pro Asn Leu Arg Met Lys Phe Gln Gly Ala Phe Arg Lys Gly Val Pro

-continued

```
                65                  70                  75                  80
Asn Pro Ile Asp Leu Leu Glu Ser Thr Leu Tyr Glu Ser Ser Val Val
                        85                  90                  95
Pro Gly Pro Lys Lys Ala Pro Met Asp Ser Leu Phe Asp Tyr Gly Thr
                        100                 105                 110
Tyr Arg His His Ser Ser Asp Asn Lys Arg Trp Arg Lys Lys Ile Ile
                        115                 120                 125
Glu Lys Gln Pro Gln Ser Pro Lys Ala Pro Ala Pro Gln Pro Pro Pro
            130                 135                 140
Ile Leu Lys Val Phe Asn Arg Pro Ile Leu Phe Asp Ile Val Ser Arg
145                 150                 155                 160
Gly Ser Thr Ala Asp Leu Asp Gly Leu Leu Pro Phe Leu Leu Thr His
                    165                 170                 175
Lys Lys Arg Leu Thr Asp Glu Glu Phe Arg Glu Pro Ser Thr Gly Lys
                180                 185                 190
Thr Cys Leu Pro Lys Ala Leu Leu Asn Leu Ser Asn Gly Arg Asn Asp
            195                 200                 205
Thr Ile Pro Val Leu Leu Asp Ile Ala Glu Arg Thr Gly Asn Met Arg
        210                 215                 220
Glu Phe Ile Asn Ser Pro Phe Arg Asp Ile Tyr Tyr Arg Gly Gln Thr
225                 230                 235                 240
Ala Leu His Ile Ala Ile Glu Arg Arg Cys Lys His Tyr Val Glu Leu
                    245                 250                 255
Leu Val Ala Gln Gly Ala Asp Val His Ala Gln Ala Arg Gly Arg Phe
                260                 265                 270
Phe Gln Pro Lys Asp Glu Gly Gly Tyr Phe Tyr Phe Gly Glu Leu Pro
            275                 280                 285
Leu Ser Leu Ala Ala Cys Thr Asn Gln Pro His Ile Val Asn Tyr Leu
        290                 295                 300
Thr Glu Asn Pro His Lys Lys Ala Asp Met Arg Arg Gln Asp Ser Arg
305                 310                 315                 320
Gly Asn Thr Val Leu His Ala Leu Val Ala Ile Ala Asp Asn Thr Arg
                    325                 330                 335
Glu Asn Thr Lys Phe Val Thr Lys Met Tyr Asp Leu Leu Leu Leu Lys
                340                 345                 350
Cys Ala Arg Leu Phe Pro Asp Ser Asn Leu Glu Ala Val Leu Asn Asn
            355                 360                 365
Asp Gly Leu Ser Pro Leu Met Met Ala Ala Lys Thr Gly Lys Ile Gly
        370                 375                 380
Ile Phe Gln His Ile Ile Arg Arg Glu Val Thr Asp Glu Asp Thr Arg
385                 390                 395                 400
His Leu Ser Arg Lys Phe Lys Asp Trp Ala Tyr Gly Pro Val Tyr Ser
                    405                 410                 415
Ser Leu Tyr Asp Leu Ser Ser Leu Asp Thr Cys Gly Glu Glu Ala Ser
                420                 425                 430
Val Leu Glu Ile Leu Val Tyr Asn Ser Lys Ile Glu Asn Arg His Glu
            435                 440                 445
Met Leu Ala Val Glu Pro Ile Asn Glu Leu Leu Arg Asp Lys Trp Arg
        450                 455                 460
Lys Phe Gly Ala Val Ser Phe Tyr Ile Asn Val Val Ser Tyr Leu Cys
465                 470                 475                 480
Ala Met Val Ile Phe Thr Leu Thr Ala Tyr Tyr Gln Pro Leu Glu Gly
                    485                 490                 495
```

Thr Pro Pro Tyr Pro Tyr Arg Thr Thr Val Asp Tyr Leu Arg Leu Ala
            500                 505                 510

Gly Glu Val Ile Thr Leu Phe Thr Gly Val Leu Phe Phe Thr Asn
            515                 520                 525

Ile Lys Asp Leu Phe Met Lys Lys Cys Pro Gly Val Asn Ser Leu Phe
530                 535                 540

Ile Asp Gly Ser Phe Gln Leu Leu Tyr Phe Ile Tyr Ser Val Leu Val
545                 550                 555                 560

Ile Val Ser Ala Ala Leu Tyr Leu Ala Gly Ile Glu Ala Tyr Leu Ala
            565                 570                 575

Val Met Val Phe Ala Leu Val Leu Gly Trp Met Asn Ala Leu Tyr Phe
            580                 585                 590

Thr Arg Gly Leu Lys Leu Thr Gly Thr Tyr Ser Ile Met Ile Gln Lys
            595                 600                 605

Ile Leu Phe Lys Asp Leu Phe Arg Phe Leu Leu Val Tyr Leu Leu Phe
            610                 615                 620

Met Ile Gly Tyr Ala Ser Ala Leu Val Ser Leu Leu Asn Pro Cys Ala
625                 630                 635                 640

Asn Met Lys Val Cys Asn Glu Asp Gln Thr Asn Cys Thr Val Pro Thr
            645                 650                 655

Tyr Pro Ser Cys Arg Asp Ser Glu Thr Phe Ser Thr Phe Leu Leu Asp
            660                 665                 670

Leu Phe Lys Leu Thr Ile Gly Met Gly Asp Leu Glu Met Leu Ser Ser
            675                 680                 685

Thr Lys Tyr Pro Val Val Phe Ile Ile Leu Leu Val Thr Tyr Ile Ile
            690                 695                 700

Leu Thr Phe Val Leu Leu Leu Asn Met Leu Ile Ala Leu Met Gly Glu
705                 710                 715                 720

Thr Val Gly Gln Val Ser Lys Glu Ser Lys His Ile Trp Lys Leu Gln
            725                 730                 735

Trp Ala Thr Thr Ile Leu Asp Ile Glu Arg Ser Phe Pro Val Phe Leu
            740                 745                 750

Arg Lys Ala Phe Arg Ser Gly Glu Met Val Thr Val Gly Lys Ser Ser
            755                 760                 765

Asp Gly Thr Pro Asp Arg Arg Trp Cys Phe Arg Val Asp Glu Val Asn
            770                 775                 780

Trp Ser His Trp Asn Gln Asn Leu Gly Ile Ile Asn Glu Asp Pro Gly
785                 790                 795                 800

Lys Asn Glu Thr Tyr Gln Tyr Tyr Gly Phe Ser His Thr Val Gly Arg
            805                 810                 815

Leu Arg Arg Asp Arg Trp Ser Ser Val Val Pro Arg Val Val Glu Leu
            820                 825                 830

Asn Lys Asn Ser Asn Pro Asp Glu Val Val Val Pro Leu Asp Ser Met
            835                 840                 845

Gly Asn Pro Arg Cys Asp Gly His Gln Gln Gly Tyr Pro Arg Lys Trp
            850                 855                 860

Arg Thr Asp Asp Ala Pro Leu
865                 870

<210> SEQ ID NO 4
<211> LENGTH: 3879
<212> TYPE: DNA
<213> ORGANISM: Homo sapiens

```
<400> SEQUENCE: 4
atcagacgcg cagaggaggc ggggccgcgg ctggtttcct gccgggggc ggctctgggc      60 cgccgagtcc cctcctcccg cccctgagga ggaggagccg ccgccacccg ccgcgcccga     120
cacccgggag gccccgccag cccgcgggag aggcccagcg ggagtcgcgg aacagcaggc     180
ccgagcccac cgcgccgggc cccggacgcc gcgcggaaaa gatgaattta caaccaattt     240
tctggattgg actgatcagt tcagtttgct gtgtgtttgc tcaaacagat gaaaatagat     300
gtttaaaagc aaatgccaaa tcatgtggag aatgtataca agcagggcca aattgtgggt     360
ggtgcacaaa ttcaacattt ttacaggaag gaatgcctac ttctgcacga tgtgatgatt     420
tagaagcctt aaaaaagaag ggttgccctc cagatgacat agaaaatccc agaggctcca     480
aagatataaa gaaaaataaa aatgtaacca accgtagcaa aggaacagca gagaagctca     540
agccagagga tattactcag atccaaccac agcagttggt tttgcgatta agatcagggg     600
agccacagac atttacatta aaattcaaga gagctgaaga ctatcccatt gacctctact     660
accttatgga cctgtcttac tcaatgaaag acgatttgga gaatgtaaaa agtcttggaa     720
cagatctgat gaatgaaatg aggaggatta cttcggactt cagaattgga tttggctcat     780
ttgtggaaaa gactgtgatg ccttacatta gcacaacacc agctaagctc aggaacccct     840
gcacaagtga acagaactgc accagcccat ttagctacaa aaatgtgctc agtcttacta     900 ataaggaga agtatttaat gaacttgttg gaaaacagcg catatctgga aatttggatt     960
ctccagaagg tggtttcgat gccatcatgc aagttgcagt tgtggatca ctgattggct    1020 ggaggaatgt tacacggctg ctggtgtttt ccacagatgc cgggtttcac tttgctggag    1080
atgggaaact tggtggcatt gttttaccaa atgatggaca atgtcacctg gaaaataata    1140
tgtacacaat gagccattat tatgattatc cttctattgc tcaccttgtc cagaaactga    1200
gtgaaaataa tattcagaca attttttgcag ttactgaaga atttcagcct gtttacaagg    1260
agctgaaaaa cttgatccct aagtcagcag taggaacatt atctgcaaat ctagcaatg    1320 taattcagtt gatcattgat gcatacaatt ccctttcctc agaagtcatt ttggaaaacg    1380
gcaaattgtc agaaggcgta acaataagtt acaaatctta ctgcaagaac ggggtgaatg    1440
gaacagggga aaatggaaga aaatgttcca atatttccat tggagatgag gttcaatttg    1500
aaattagcat aacttcaaat aagtgtccaa aaaaggattc tgacagcttt aaaattaggc    1560
ctctgggctt tacggaggaa gtagaggtta ttcttcagta catctgtgaa tgtgaatgcc    1620
aaagcgaagg catccctgaa agtcccaagt gtcatgaagg aaatgggaca tttgagtgtg    1680
gcgcgtgcag gtgcaatgaa gggcgtgttg gtagacattg tgaatgcagc acagatgaag    1740
ttaacagtga agacatggat gcttactgca ggaaagaaaa cagttcagaa atctgcagta    1800
acaatggaga gtgcgtctgc ggacagtgtg tttgtaggaa gagggataat acaaatgaaa    1860
tttattctgg caaattctgc gagtgtgata atttcaactg tgatagatcc aatggcttaa    1920
tttgtggagg aaatggtgtt tgcaagtgtc gtgtgtgtga gtgcaacccc aactacactg    1980
gcagtgcatg tgactgttct ttggatacta gtacttgtga agccagcaac ggacagatct    2040
gcaatggccg gggcatctgc gagtgtgtgt ctgtaagtg tacagatccg aagtttcaag    2100
ggcaaacgtg tgagatgtgt cagacctgcc ttggtgtctg tgctgagcat aaagaatgtg    2160
ttcagtgcag agccttcaat aaaggagaaa agaaagacac atgcacacag gaatgttcct    2220 atttaacat taccaaggta gaaagtcggg acaaattacc ccagccggtc caacctgatc    2280
ctgtgtccca ttgtaaggag aaggatgttg acgactgttg gttctatttt acgtattcag    2340
```

```
tgaatgggaa caacgaggtc atggttcatg ttgtggagaa tccagagtgt cccactggtc    2400
cagacatcat tccaattgta gctggtgtgg ttgctggaat tgttcttatt ggccttgcat    2460
tactgctgat atggaagctt ttaatgataa ttcatgacag aagggagttt gctaaatttg    2520
aaaaggagaa aatgaatgcc aaatgggaca cgggtgaaaa tcctatttat aagagtgccg    2580
taacaactgt ggtcaatccg aagtatgagg gaaaatgagt actgcccgtg caaatcccac    2640
aacactgaat gcaaagtagc aatttccata gtcacagtta ggtagcttta gggcaatatt    2700
gccatggttt tactcatgtg caggttttga aaatgtacaa tatgtataat ttttaaaatg    2760
ttttattatt ttgaaaataa tgttgtaatt catgccaggg actgacaaaa gacttgagac    2820
aggatggtta ctcttgtcag ctaaggtcac attgtgcctt tttgaccttt tcttcctgga    2880
ctattgaaat caagcttatt ggattaagtg atatttctat agcgattgaa agggcaatag    2940
ttaaagtaat gagcatgatg agagtttctg ttaatcatgt attaaaactg attttttagct   3000 ttacaaatat gtcagtttgc agttatgcag aatccaaagt aaatgtcctg ctagctagtt    3060
aaggattgtt ttaaatctgt tattttgcta tttgcctgtt agacatgact gatgacatat    3120
ctgaaagaca agtatgttga gagttgctgg tgtaaaatac gtttgaaata gttgatctac    3180
aaaggccatg ggaaaaattc agagagttag gaaggaaaaa ccaatagctt taaaacctgt    3240
gtgccatttt aagagttact taatgtttgg taacttttat gccttcactt tacaaattca    3300
agccttagat aaaagaaccg agcaatttc tgctaaaaag tccttgattt agcactattt     3360
acatacaggc catactttac aaagtatttg ctgaatgggg accttttgag ttgaatttat    3420
tttattattt ttattttgtt taatgtctgg tgctttctgt cacctcttct aatcttttaa    3480
tgtatttgtt tgcaatttg gggtaagact tttttatga gtacttttc tttgaagttt       3540 tagcggtcaa tttgcctttt taatgaacat gtgaagttat actgtggcta tgcaacagct    3600
ctcacctacg cgagtcttac tttgagttag tgccataaca gaccactgta tgtttacttc    3660
tcaccatttg agttgcccat cttgtttcac actagtcaca ttcttgtttt aagtgccttt    3720
agttttaaca gttcactttt tacagtgcta tttactgaag ttatttatta aatatgccta    3780
aaatacttaa atcggatgtc ttgactctga tgtatttat caggttgtgt gcatgaaatt     3840
tttatagatt aaagaagttg aggaaaagca aaaaaaaa                            3879
```

<210> SEQ ID NO 5
<211> LENGTH: 798
<212> TYPE: PRT
<213> ORGANISM: Homo sapiens

<400> SEQUENCE: 5

```
Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
            20                  25                  30

Lys Ser Cys Gly Glu Cys Ile Gln Ala Gly Pro Asn Cys Gly Trp Cys
        35                  40                  45

Thr Asn Ser Thr Phe Leu Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95
```

```
Asn Arg Ser Lys Gly Thr Ala Glu Lys Leu Lys Pro Glu Asp Ile Thr
                100                 105                 110

Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
        130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
        195                 200                 205

Ser Glu Gln Asn Cys Thr Ser Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
        275                 280                 285

Lys Leu Gly Gly Ile Val Leu Pro Asn Asp Gly Gln Cys His Leu Glu
290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510

Asp Ala Tyr Cys Arg Lys Glu Asn Ser Ser Glu Ile Cys Ser Asn Asn
```

Gly Glu Cys Val Cys Gly Gln Cys Val Cys Arg Lys Arg Asp Asn Thr
        515                 520                 525
530

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 6
<211> LENGTH: 2350
<212> TYPE: DNA
<213> ORGANISM: Homo sapiens

<400> SEQUENCE: 6
agttccaggg aaggagggcg tagacaaagc gccacctgaa cttgcggcgc gaaaaaggcg      60
cgcatgcgtc ctacgggagc gtgctggctc accgaccgca ttgcggcttg gttttctcac     120
ccagtgcatg tggcaggagc ggtgagatca ctgcctcacg gcgatcctgg actgacggtc     180
acgactgcct accctctaac cctgttctga gctgccccct gcccacacac cccaaacctg     240
tgtgcaggat ccgcctccat ggagctacag cctcctgaag cctcgatcgc cgtcgtgtcg     300
attccgcgcc agttgcctgg ctcacattcg gaggctggtg tccagggtct cagcgcgggg     360
gacgactcag agacggggtc tgactgtgtt acccaggctg tcttcaact cttggcctca      420 agtgatcctc ctgccttagc ttccaagaat gctgaggtta cagtagaaac ggggtttcac     480
catgttagcc aggctgatat tgaattcctg acctcaattg atccgactgc ctcggcctcc     540

```
ggaagtgctg ggattacagg caccatgagc caggacaccg aggtggatat gaaggaggtg    600
gagctgaatg agttagagcc cgagaagcag ccgatgaacg cggcgtctgg ggcggccatg    660
tccctggcgg gagccgagaa gaatggtctg gtgaagatca aggtggcgga agacgaggcg    720
gaggcggcag ccgcggctaa gttcacgggc ctgtccaagg aggagctgct gaaggtggca    780
ggcagccccg gctgggtacg cacccgctgg gcactgctgc tgctcttctg gctcggctgg    840
ctcggcatgc ttgctggtgc cgtggtcata atcgtgcgag cgccgcgttg tcgcgagcta    900
ccggcgcaga agtggtggca cacgggcgcc ctctaccgca tcggcgacct tcaggccttc    960
cagggccacg cgcgggcaa cctggcgggt ctgaaggggc gtctcgatta cctgagctct   1020
ctgaaggtga agggccttgt gctgggtcca attcacaaga accagaagga tgatgtcgct   1080
cagactgact tgctgcagat cgaccccaat tttggctcca aggaagattt tgacagtctc   1140
ttgcaatcgg ctaaaaaaaa gagcatccgt gtcattctgg accttactcc caactaccgg   1200
ggtgagaact cgtggttctc cactcaggtt gacactgtgg ccaccaaggt gaaggatgct   1260
ctggagtttt ggctgcaagc tggcgtggat gggttccagg ttcgggacat agagaatctg   1320
aaggatgcat cctcattctt ggctgagtgg caaaatatca ccaagggctt cagtgaagac   1380
aggctcttga ttgcggggac taactcctcc gaccttcagc agatcctgag cctactcgaa   1440
tccaacaaag acttgctgtt gactagctca tacctgtctg attctggttc tactggggag   1500
catacaaaat ccctagtcac acagtatttg aatgccactg caatcgctg gtgcagctgg   1560
agtttgtctc aggcaaggct cctgacttcc ttcttgccgg ctcaacttct ccgactctac   1620
cagctgatgc tcttcaccct gccagggacc cctgttttca gctacgggga tgagattggc   1680
ctggatgcag ctgcccttcc tggacagcct atggaggctc cagtcatgct gtgggatgag   1740
tccagcttcc ctgacatccc aggggctgta agtgccaaca tgactgtgaa gggccagagt   1800
gaagaccctg gctccctcct ttccttgttc cggcggctga gtgaccagcg gagtaaggag   1860
cgctccctac tgcatgggga cttccacgcg ttctccgctg ggcctggact cttctcctat   1920
atccgccact gggaccagaa tgagcgtttt ctggtagtgc ttaactttgg ggatgtgggc   1980
ctctcggctg gactgcaggc ctccgacctg cctgccagcg ccagcctgcc agccaaggct   2040
gacctcctgc tcagcaccca gccaggccgt gaggagggct cccctcttga gctggaacgc   2100
ctgaaactgg agcctcacga agggctgctg ctccgcttcc cctacgcggc ctgacttcag   2160
cctgacatgg acccactacc cttctccttt ccttcccagg ccctttggct tctgatttt    2220
ctcttttta aaacaaaca aacaaactgt tgcagattat gagtgaaccc ccaaataggg    2280
tgttttctgc cttcaaataa aagtcacccc tgcatggtga agtcttccct ctgcttctct   2340
cataaaaaaa                                                          2350
```

<210> SEQ ID NO 7
<211> LENGTH: 631
<212> TYPE: PRT
<213> ORGANISM: Homo sapiens

<400> SEQUENCE: 7

Met Glu Leu Gln Pro Pro Glu Ala Ser Ile Ala Val Val Ser Ile Pro
1               5                   10                  15

Arg Gln Leu Pro Gly Ser His Ser Glu Ala Gly Val Gln Gly Leu Ser
            20                  25                  30

Ala Gly Asp Asp Ser Glu Thr Gly Ser Asp Cys Val Thr Gln Ala Gly
        35                  40                  45

-continued

```
Leu Gln Leu Leu Ala Ser Ser Asp Pro Pro Ala Leu Ala Ser Lys Asn
 50                  55                  60
Ala Glu Val Thr Val Glu Thr Gly Phe His His Val Ser Gln Ala Asp
 65                  70                  75                  80
Ile Glu Phe Leu Thr Ser Ile Asp Pro Thr Ala Ser Ala Ser Gly Ser
                 85                  90                  95
Ala Gly Ile Thr Gly Thr Met Ser Gln Asp Thr Glu Val Asp Met Lys
            100                 105                 110
Glu Val Glu Leu Asn Glu Leu Glu Pro Glu Lys Gln Pro Met Asn Ala
        115                 120                 125
Ala Ser Gly Ala Ala Met Ser Leu Ala Gly Ala Glu Lys Asn Gly Leu
130                 135                 140
Val Lys Ile Lys Val Ala Glu Asp Glu Ala Glu Ala Ala Ala Ala Ala
145                 150                 155                 160
Lys Phe Thr Gly Leu Ser Lys Glu Glu Leu Leu Lys Val Ala Gly Ser
                165                 170                 175
Pro Gly Trp Val Arg Thr Arg Trp Ala Leu Leu Leu Phe Trp Leu
            180                 185                 190
Gly Trp Leu Gly Met Leu Ala Gly Ala Val Val Ile Ile Val Arg Ala
        195                 200                 205
Pro Arg Cys Arg Glu Leu Pro Ala Gln Lys Trp Trp His Thr Gly Ala
210                 215                 220
Leu Tyr Arg Ile Gly Asp Leu Gln Ala Phe Gln Gly His Gly Ala Gly
225                 230                 235                 240
Asn Leu Ala Gly Leu Lys Gly Arg Leu Asp Tyr Leu Ser Ser Leu Lys
                245                 250                 255
Val Lys Gly Leu Val Leu Gly Pro Ile His Lys Asn Gln Lys Asp Asp
            260                 265                 270
Val Ala Gln Thr Asp Leu Leu Gln Ile Asp Pro Asn Phe Gly Ser Lys
        275                 280                 285
Glu Asp Phe Asp Ser Leu Leu Gln Ser Ala Lys Lys Ser Ile Arg
290                 295                 300
Val Ile Leu Asp Leu Thr Pro Asn Tyr Arg Gly Glu Asn Ser Trp Phe
305                 310                 315                 320
Ser Thr Gln Val Asp Thr Val Ala Thr Lys Val Lys Asp Ala Leu Glu
                325                 330                 335
Phe Trp Leu Gln Ala Gly Val Asp Gly Phe Gln Val Arg Asp Ile Glu
            340                 345                 350
Asn Leu Lys Asp Ala Ser Ser Phe Leu Ala Glu Trp Gln Asn Ile Thr
        355                 360                 365
Lys Gly Phe Ser Glu Asp Arg Leu Leu Ile Ala Gly Thr Asn Ser Ser
370                 375                 380
Asp Leu Gln Gln Ile Leu Ser Leu Leu Glu Ser Asn Lys Asp Leu Leu
385                 390                 395                 400
Leu Thr Ser Ser Tyr Leu Ser Asp Ser Gly Ser Thr Gly Glu His Thr
                405                 410                 415
Lys Ser Leu Val Thr Gln Tyr Leu Asn Ala Thr Gly Asn Arg Trp Cys
            420                 425                 430
Ser Trp Ser Leu Ser Gln Ala Arg Leu Leu Thr Ser Phe Leu Pro Ala
        435                 440                 445
Gln Leu Leu Arg Leu Tyr Gln Leu Met Leu Phe Thr Leu Pro Gly Thr
450                 455                 460
Pro Val Phe Ser Tyr Gly Asp Glu Ile Gly Leu Asp Ala Ala Ala Leu
```

```
                465                 470                 475                 480
        Pro Gly Gln Pro Met Glu Ala Pro Val Met Leu Trp Asp Glu Ser Ser
                            485                 490                 495

Phe Pro Asp Ile Pro Gly Ala Val Ser Ala Asn Met Thr Val Lys Gly
                        500                 505                 510

Gln Ser Glu Asp Pro Gly Ser Leu Leu Ser Leu Phe Arg Arg Leu Ser
                    515                 520                 525

Asp Gln Arg Ser Lys Glu Arg Ser Leu Leu His Gly Asp Phe His Ala
                530                 535                 540

Phe Ser Ala Gly Pro Gly Leu Phe Ser Tyr Ile Arg His Trp Asp Gln
        545                 550                 555                 560

Asn Glu Arg Phe Leu Val Val Leu Asn Phe Gly Asp Val Gly Leu Ser
                        565                 570                 575

Ala Gly Leu Gln Ala Ser Asp Leu Pro Ala Ser Ala Ser Leu Pro Ala
                    580                 585                 590

Lys Ala Asp Leu Leu Leu Ser Thr Gln Pro Gly Arg Glu Glu Gly Ser
                595                 600                 605

Pro Leu Glu Leu Glu Arg Leu Lys Leu Glu Pro His Glu Gly Leu Leu
            610                 615                 620

Leu Arg Phe Pro Tyr Ala Ala
        625                 630

<210> SEQ ID NO 8
<211> LENGTH: 4543
<212> TYPE: DNA
<213> ORGANISM: Homo sapiens

<400> SEQUENCE: 8
cggcgggcgg cgcgcacact gctcgctggg ccgcggctcc cgggtgtccc aggcccggcc      60
ggtgcgcaga gcatggcggg tgcgggcccg aagcggcgcg cgctagcggc gccggcggcc     120
gaggagaagg aagaggcgcg ggagaagatg ctggccgcca agagcgcgga cggctcggcg     180
ccggcaggcg agggcgaggg cgtgaccctg cagcggaaca tcacgctgct caacggcgtg     240
gccatcatcg tggggaccat tatcggctcg ggcatcttcg tgacgcccac gggcgtgctc     300
aaggaggcag gctcgccggg gctggcgctg gtggtgtggg ccgcgtgcgg cgtcttctcc     360
atcgtgggcg cgctctgcta cgcggagctc ggcaccacca tctccaaatc gggcggcgac     420
tacgcctaca tgctggaggt ctacggctcg ctgcccgcct cctcaagct ctggatcgag     480 ctgctcatca tccggccttc atcgcagtac atcgtggccc tggtcttcgc cacctacctg     540
ctcaagccgc tcttccccac ctgcccggtg cccgaggagg cagccaagct cgtggcctgc     600
tctctgcgtg ctgctgctca cggccgtgaac tgctacagcg tgaaggccgc caccgggtc     660 caggatgcct ttgccgccgc caagctcctg gccctggccc tgatcatcct gctgggcttc     720
gtccagatcg gaagggtga tgtgtccaat ctagatccca acttctcatt tgaaggcacc     780
aaactggatg tggggaacat tgtgctggca ttatacagcg gcctctttgc ctatggagga     840
tggaattact tgaatttcgt cacagaggaa atgatcaacc cctacagaaa cctgcccctg     900
gccatcatca tctccctgcc catcgtgacg ctggtgtacg tgctgaccaa cctgcctac      960 ttcaccaccc tgtccaccga gcagatgctg tcgtccgagg ccgtggccgt ggacttcggg    1020
aactatcacc tgggcgtcat gtcctggatc atcccgtct tcgtgggcct gtcctgcttc    1080
ggctccgtca tgggtccct gttcacatcc tccaggctct cttcgtggg gtcccggaa      1140 ggccacctgc cctccatcct ctccatgatc cacccacagc tcctcacccc cgtgccgtcc    1200
```

```
ctcgtgttca cgtgtgtgat gacgctgctc tacgccttct ccaaggacat cttctccgtc    1260
atcaacttct tcagcttctt caactggctc tgcgtggccc tggccatcat cggcatgatc    1320
tggctgcgcc acagaaagcc tgagcttgag cggcccatca aggtgaacct ggccctgcct    1380
gtgttcttca tcctggcctg cctcttcctg atcgccgtct ccttctggaa gacacccgtg    1440
gagtgtggca tcggcttcac catcatcctc agcgggctgc ccgtctactt cttcggggtc    1500
tggtggaaaa acaagcccaa gtggctcctc cagggcatct tctccacgac cgtcctgtgt    1560
cagaagctca tgcaggtggt cccccaggag acatagccag gaggccgagt ggctgccgga    1620
ggagcatgcg cagaggccag ttaaagtaga tcacctcctc gaacccactc cggttccccg    1680
caacccacag ctcagctgcc catcccagtc cctcgccgtc cctcccaggt cgggcagtgg    1740
aggctgctgt gaaaactctg gtacgaatct catccctcaa ctgagggcca gggacccagg    1800
tgtgcctgtg ctcctgccca ggagcagctt ttggtctcct tgggcccttt ttccctttccc    1860 tcctttgttt acttatatat atatttttttt taaacttaaa ttttgggtca acttgacacc    1920
actaagatga tttttttaagg agctggggga aggcaggagc cttcctttct cctgccccaa    1980
gggcccagac cctgggcaaa cagagctact gagacttgga acctcattgc taccacagac    2040
ttgcactgaa gccggacagc tgcccagaca catgggcttg tgacattcgt gaaaaccaac    2100
cctgtgggct tatgtctctg ccttagggtt tgcagagtgg aaactcagcc gtagggtggc    2160
actgggaggg ggtgggggat ctgggcaagg tgggtgattc ctcccaggag gtgcttgagg    2220
ccccgatgga ctcctgacca taatcctagc cccgagacac catcctgagc cagggaacag    2280
ccccagggtt gggggggtgcc ggcatctccc ctagctcacc aggcctggcc tctgggcagt    2340
gtggcctctt ggctatttct gtgtccagtt ttggaggctg agttctggtt catgcagaca    2400
aagccctgtc cttcagtctt ctagaaacag agacaagaaa ggcagacaca ccgcggccag    2460
gcacccatgt gggcgcccac cctgggctcc acacagcagt gtccctgcc ccagaggtcg    2520 cagctaccct cagcctccaa tgcattggcc tctgtaccgc ccggcagccc cttctggccg    2580
gtgctgggtt cccactcccg gcctaggcac ctccccgctc tccctgtcac gctcatgtcc    2640
tgtcctggtc ctgatgcccg ttgtctagga gacagagcca agcactgctc acgtctctgc    2700
cgcctgcgtt tggaggcccc tgggctctca cccagtcccc accgcctgc agagagggaa    2760 ctagggcacc ccttgtttct gttgttcccg tgaattttttt tcgctatggg aggcagccga    2820
ggcctggcca atgcggccca ctttcctgag ctgtcgctgc ctccatggca gcagccaggg    2880 accccccagaa caagaagacc ccgcaggatc cctcctgagc tcgggggggct ctgccttctc    2940 aggccccggg cttcccttct ccccagccag aggtggagcc aagtggtcca gcgtcactcc    3000
agtgctcagc tgtggctgga ggagctgccc tgtggcacag ccctgagtgt cccaagccgg    3060
gagccaacga agccggacac ggcttcactg accagcggct gctcaagccg caagctctca    3120
gcaagtgccc agtggagcct gccgcccccg cctgggcacc gggacccccct caccatccag    3180 tgggcccgga gaaacctgat gaacagtttg gggactcagg accagatgtc cgtctctctt    3240
gcttgaggaa tgaagacctt tattcacccc tgccccgttg cttcccgctg cacatggaca    3300
gacttcacag cgtctgctca taggacctgc atccttcctg gggacgaatt ccactcgtcc    3360
aagggacagc ccacggtctg gaggccgagg accaccagca ggcaggtgga ctgactgtgt    3420
tgggcaagac ctcttccctc tgggcctgtt ctcttggctg caaataagga cagcagctgc    3480
tgccccacct gcctggtgca ttgctgtgtg aatccaggag gcagtggaca tcgtaggcag    3540
```

```
ccacggcccc gggtccagga gaagtgctcc ctggaggcac gcaccactgc ttcccactgg   3600
ggccggcggg gcccacgcac gacgtcagcc tcttaccttc ccgcctcggc tagggtcct   3660
cgggatgccg ttctgttcca acctcctgct ctgggacgtg acatgcctc aaggatacag   3720
ggagccggcg gcctctcgac ggcacgcact tgcctgttgg ctgctgcggc tgtgggcgag   3780
catgggggct gccagcgtct gttgtggaaa gtagctgcta gtgaaatggc tggggccgct   3840
ggggtccgtc ttcacactgc gcaggtctct tctgggcgtc tgagctgggg tgggagctcc   3900
tccgcagaag gttggtgggg ggtccagtct gtgatccttg gtgctgtgtg ccccactcca   3960
gcctggggac cccacttcag aaggtagggg ccgtgtcccg cggtgctgac tgaggcctgc   4020
ttccccctcc ccctcctgct gtgctggaat tccacaggga ccagggccac cgcagggac   4080
tgtctcagaa gacttgattt ttccgtccct ttttctccac actccactga caaacgtccc   4140
cagcggtttc cacttgtggg cttcaggtgt tttcaagcac aacccaccac aacaagcaag   4200
tgcattttca gtcgttgtgc ttttttgttt tgtgctaacg tcttactaat ttaaagatgc   4260
tgtcggcacc atgtttattt atttccagtg gtcatgctca gccttgctgc tctgcgtggc   4320
gcaggtgcca tgcctgctcc ctgtctgtgt cccagccacg cagggccatc cactgtgacg   4380
tcggccgacc aggctggaca ccctctgccg agtaatgacg tgtgtggctg ggaccttctt   4440
tattctgtgt taatggctaa cctgttacac tgggctgggt tgggtagggt gttctggctt   4500
ttttgtgggg ttttatttt taagaaaaca ctcaatcatc cta                      4543
```

<210> SEQ ID NO 9
<211> LENGTH: 507
<212> TYPE: PRT
<213> ORGANISM: Homo sapiens

<400> SEQUENCE: 9

```
Met Ala Gly Ala Gly Pro Lys Arg Arg Ala Leu Ala Ala Pro Ala Ala
1               5                   10                  15

Glu Glu Lys Glu Glu Ala Arg Glu Lys Met Leu Ala Ala Lys Ser Ala
            20                  25                  30

Asp Gly Ser Ala Pro Ala Gly Glu Gly Glu Gly Val Thr Leu Gln Arg
        35                  40                  45

Asn Ile Thr Leu Leu Asn Gly Val Ala Ile Ile Val Gly Thr Ile Ile
    50                  55                  60

Gly Ser Gly Ile Phe Val Thr Pro Thr Gly Val Leu Lys Glu Ala Gly
65                  70                  75                  80

Ser Pro Gly Leu Ala Leu Val Val Trp Ala Ala Cys Gly Val Phe Ser
                85                  90                  95

Ile Val Gly Ala Leu Cys Tyr Ala Glu Leu Gly Thr Thr Ile Ser Lys
            100                 105                 110

Ser Gly Gly Asp Tyr Ala Tyr Met Leu Glu Val Tyr Gly Ser Leu Pro
        115                 120                 125

Ala Phe Leu Lys Leu Trp Ile Glu Leu Leu Ile Ile Arg Pro Ser Ser
    130                 135                 140

Gln Tyr Ile Val Ala Leu Val Phe Ala Thr Tyr Leu Leu Lys Pro Leu
145                 150                 155                 160

Phe Pro Thr Cys Pro Val Pro Glu Glu Ala Ala Lys Leu Val Ala Cys
                165                 170                 175

Leu Cys Val Leu Leu Leu Thr Ala Val Asn Cys Tyr Ser Val Lys Ala
            180                 185                 190

Ala Thr Arg Val Gln Asp Ala Phe Ala Ala Ala Lys Leu Leu Ala Leu
```

```
                195                 200                 205
Ala Leu Ile Ile Leu Leu Gly Phe Val Gln Ile Gly Lys Gly Asp Val
210                 215                 220

Ser Asn Leu Asp Pro Asn Phe Ser Phe Glu Gly Thr Lys Leu Asp Val
225                 230                 235                 240

Gly Asn Ile Val Leu Ala Leu Tyr Ser Gly Leu Phe Ala Tyr Gly Gly
                245                 250                 255

Trp Asn Tyr Leu Asn Phe Val Thr Glu Glu Met Ile Asn Pro Tyr Arg
            260                 265                 270

Asn Leu Pro Leu Ala Ile Ile Ile Ser Leu Pro Ile Val Thr Leu Val
        275                 280                 285

Tyr Val Leu Thr Asn Leu Ala Tyr Phe Thr Thr Leu Ser Thr Glu Gln
    290                 295                 300

Met Leu Ser Ser Glu Ala Val Ala Val Asp Phe Gly Asn Tyr His Leu
305                 310                 315                 320

Gly Val Met Ser Trp Ile Ile Pro Val Phe Val Gly Leu Ser Cys Phe
                325                 330                 335

Gly Ser Val Asn Gly Ser Leu Phe Thr Ser Ser Arg Leu Phe Phe Val
            340                 345                 350

Gly Ser Arg Glu Gly His Leu Pro Ser Ile Leu Ser Met Ile His Pro
        355                 360                 365

Gln Leu Leu Thr Pro Val Pro Ser Leu Val Phe Thr Cys Val Met Thr
    370                 375                 380

Leu Leu Tyr Ala Phe Ser Lys Asp Ile Phe Ser Val Ile Asn Phe Phe
385                 390                 395                 400

Ser Phe Phe Asn Trp Leu Cys Val Ala Leu Ala Ile Ile Gly Met Ile
                405                 410                 415

Trp Leu Arg His Arg Lys Pro Glu Leu Glu Arg Pro Ile Lys Val Asn
            420                 425                 430

Leu Ala Leu Pro Val Phe Phe Ile Leu Ala Cys Leu Phe Leu Ile Ala
        435                 440                 445

Val Ser Phe Trp Lys Thr Pro Val Glu Cys Gly Ile Gly Phe Thr Ile
    450                 455                 460

Ile Leu Ser Gly Leu Pro Val Tyr Phe Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
            500                 505

<210> SEQ ID NO 10
<211> LENGTH: 9
<212> TYPE: PRT
<213> ORGANISM: Human immunodeficiency virus 1

<400> SEQUENCE: 10

Arg Lys Lys Arg Arg Gln Arg Arg Arg
1               5

<210> SEQ ID NO 11
<211> LENGTH: 13
<212> TYPE: PRT
<213> ORGANISM: Human immunodeficiency virus 1

<400> SEQUENCE: 11

Gly Arg Lys Lys Arg Arg Gln Arg Arg Arg Thr Pro Gln
```

```
<210> SEQ ID NO 12
<211> LENGTH: 11
<212> TYPE: PRT
<213> ORGANISM: Human immunodeficiency virus 1

<400> SEQUENCE: 12

Tyr Gly Arg Lys Lys Arg Arg Gln Arg Arg Arg
1               5                   10

<210> SEQ ID NO 13
<211> LENGTH: 26
<212> TYPE: PRT
<213> ORGANISM: Unknown
<220> FEATURE:
<223> OTHER INFORMATION: Description of Unknown: Kaposi fibroblast
      growth factor peptide

<400> SEQUENCE: 13

Ala Ala Val Ala Leu Leu Pro Ala Val Leu Leu Ala Leu Leu Ala Pro
1               5                   10                  15

Val Gln Arg Lys Arg Gln Lys Leu Met Pro
            20                  25

<210> SEQ ID NO 14
<211> LENGTH: 17
<212> TYPE: PRT
<213> ORGANISM: Caiman crocodylus

<400> SEQUENCE: 14

Met Gly Leu Gly Leu His Leu Leu Val Leu Ala Ala Ala Leu Gln Gly
1               5                   10                  15

Ala

<210> SEQ ID NO 15
<211> LENGTH: 23
<212> TYPE: PRT
<213> ORGANISM: Human immunodeficiency virus 1

<400> SEQUENCE: 15

Gly Ala Leu Phe Leu Gly Phe Leu Gly Ala Ala Gly Ser Thr Met Gly
1               5                   10                  15

Ala Pro Lys Ser Lys Arg Lys
            20

<210> SEQ ID NO 16
<211> LENGTH: 16
<212> TYPE: PRT
<213> ORGANISM: Drosophila sp.
<220> FEATURE:
<223> OTHER INFORMATION: C-term amide

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 24
<212> TYPE: PRT
<213> ORGANISM: Influenza virus

<400> SEQUENCE: 17

Gly Leu Phe Glu Ala Ile Ala Gly Phe Ile Glu Asn Gly Trp Glu Gly
```

```
1               5                   10                  15
Met Ile Asp Gly Gly Gly Tyr Cys
            20

<210> SEQ ID NO 18
<211> LENGTH: 27
<212> TYPE: PRT
<213> ORGANISM: Unknown
<220> FEATURE:
<223> OTHER INFORMATION: Description of Unknown: Transportan A peptide

<400> SEQUENCE: 18

Gly Trp Thr Leu Asn Ser Ala Gly Tyr Leu Leu Gly Lys Ile Asn Leu
1               5                   10                  15
Lys Ala Leu Ala Ala Leu Ala Lys Lys Ile Leu
            20                  25

<210> SEQ ID NO 19
<211> LENGTH: 9
<212> TYPE: PRT
<213> ORGANISM: Unknown
<220> FEATURE:
<223> OTHER INFORMATION: Description of Unknown: Pre-S-peptide
<220> FEATURE:
<221> NAME/KEY: MOD_RES
<222> LOCATION: (1)..(1)
<223> OTHER INFORMATION: May or may not be present

<400> SEQUENCE: 19

Ser Asp His Gln Leu Asn Pro Ala Phe
1               5

<210> SEQ ID NO 20
<211> LENGTH: 9
<212> TYPE: PRT
<213> ORGANISM: Unknown
<220> FEATURE:
<223> OTHER INFORMATION: Description of Unknown: Somatostatin peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Optional D isomer for stability
<220> FEATURE:
<221> NAME/KEY: MOD_RES
<222> LOCATION: (5)..(5)
<223> OTHER INFORMATION: Optional D isomer for stability

<400> SEQUENCE: 20

Ser Phe Cys Tyr Trp Lys Thr Cys Thr
1               5

<210> SEQ ID NO 21
<211> LENGTH: 19
<212> TYPE: RNA
<213> ORGANISM: Homo sapiens

<400> SEQUENCE: 21
gaauggucug gugaagauc                                                19

<210> SEQ ID NO 22
<211> LENGTH: 19
<212> TYPE: RNA
<213> ORGANISM: Homo sapiens
```

-continued

<400> SEQUENCE: 22
gaucuucacc agaccauuc                                                 19

<210> SEQ ID NO 23
<211> LENGTH: 51
<212> TYPE: PRT
<213> ORGANISM: Homo sapiens

<400> SEQUENCE: 23

Lys Phe Thr Gly Leu Ser Lys Glu Glu Leu Leu Lys Val Ala Gly Ser
1               5                   10                  15

Pro Gly Trp Val Arg Thr Arg Trp Ala Leu Leu Leu Leu Phe Trp Leu
            20                  25                  30

Gly Trp Leu Gly Met Leu Ala Gly Ala Val Val Ile Ile Val Arg Ala
        35                  40                  45

Pro Arg Cys
    50

<210> SEQ ID NO 24
<211> LENGTH: 51
<212> TYPE: PRT
<213> ORGANISM: Mus sp.

<400> SEQUENCE: 24

Lys Phe Thr Gly Leu Ser Lys Glu Glu Leu Leu Lys Val Ala Gly Ser
1               5                   10                  15

Pro Gly Trp Val Arg Thr Arg Trp Ala Leu Leu Leu Leu Phe Trp Leu
            20                  25                  30

Gly Trp Leu Gly Met Leu Ala Gly Ala Val Val Ile Ile Val Arg Ala
        35                  40                  45

Pro Arg Cys
    50

<210> SEQ ID NO 25
<211> LENGTH: 51
<212> TYPE: PRT
<213> ORGANISM: Xenopus sp.

<400> SEQUENCE: 25

Lys Phe Thr Gly Leu Ser Lys Glu Glu Leu Leu Arg Val Ala Gly Thr
1               5                   10                  15

Pro Thr Trp Val Arg Val Arg Trp Ala Leu Leu Leu Leu Phe Trp Leu
            20                  25                  30

Gly Trp Ala Gly Met Leu Ala Gly Ala Val Val Ile Ile Val Gln Ala
        35                  40                  45

Pro Arg Cys
    50

<210> SEQ ID NO 26
<211> LENGTH: 51
<212> TYPE: PRT
<213> ORGANISM: Drosophila sp.

<400> SEQUENCE: 26

Ala Phe Thr Gly Met Ser Lys Glu Glu Leu Met Lys Tyr Ala Asn Asp
1               5                   10                  15

```
Pro Phe Trp Val Arg Leu Arg Trp Ile Phe Phe Val Cys Phe Trp Ala
            20                  25                  30

Ile Trp Val Gly Met Leu Val Gly Ala Ile Leu Ile Ile Gly Ala
            35                  40                  45

Pro Lys Cys
    50
```

METHODS AND COMPOSITIONS FOR THE INHIBITION OF TRPV4

CROSS-REFERENCE TO RELATED APPLICATIONS

This application is a continuation under 35 U.S.C. § 120 of U.S. application Ser. No. 14/900,265 filed Dec. 21, 2015, which is a 35 U.S.C. § 371 National Phase Entry Application of International Application No. PCT/US2014/043785 filed Jun. 24, 2014, which designates the U.S., and which claims benefit under 35 U.S.C. § 119(e) of U.S. Provisional Application No. 61/838,488 filed Jun. 24, 2013, the contents of which are incorporated herein by reference in their entirety.

GOVERNMENT SUPPORT

This invention was made with federal funding under Grant Nos. CA045548 and CA074540 awarded by the National Institutes of Health. The U.S. government has certain rights in the invention.

SEQUENCE LISTING

The instant application contains a Sequence Listing which has been submitted electronically in ASCII format and is hereby incorporated by reference in its entirety. Said ASCII copy, created on Jun. 20, 2014, is named 701039-077711-PCT_SL.txt and is 48,903 bytes in size.

TECHNICAL FIELD

The technology described herein relates to methods and compositions for the treatment of diseases involving TRPV4 signaling, e.g. pulmonary edema.

BACKGROUND

TRPV4 is a transmembrane protein that is expressed in many tissue types throughout the body and which has been implicated in a number of diverse diseases, ranging from pulmonary edema, to inflammation, to hypertension, to hyperalgesia. It also can regulate vascular permeability and so may play an important role in development of edema, and provide a mechanism to modulate drug delivery to tumors or across the blood-brain barrier. TRPV4 can be activated both by chemical inputs (e.g. ligand binding) and mechanical inputs (e.g. physical strains and stresses on the cell). While inhibitors of the chemical activation of TRPV4 are known (e.g. GSK2193874), there is no existing means of specifically inhibiting the mechanical activation of TRPV4.

SUMMARY

As described herein, the inventors have identified a domain of CD98 which is required for the formation of a CD98-TRPV4-β1integrin complex which specifically mediates the mechanically-induced activation of TRPV4. Accordingly, described herein are compositions and methods relating to disrupting this complex and thereby inhibiting mechanical induction of TRPV4 activity. TRPV4 plays a role in a number of diseases and inhibition of TRPV4 therefor has therapeutic use in the treatment of those diseases, including, e.g. pulmonary edema, in addition to potentially providing ways to modulate drug delivery across vascular barriers.

In one aspect, described herein is an isolated polypeptide comprising the sequence of SEQ ID NO: 1. In some embodiments, the polypeptide is a recombinant polypeptide. In some embodiments, the polypeptide can further comprise a cell-penetrating agent. In some embodiments, the cell-penetrating agent is selected from the group consisting of TAT polypeptide or a lipid protein delivery reagent, e.g, BIO-PORTER™.

In one aspect, described herein is an isolated nucleic acid encoding the polypeptide described herein. In one aspect, described herein is a vector comprising the isolated nucleic acid described herein.

In one aspect, described herein is a pharmaceutical composition comprising the polypeptide, the nucleic acid, or the vector described herein and a pharmaceutically acceptable carrier.

In one aspect, described herein is a method of inhibiting the mechanically-dependent activation of TRPV4, the method comprising administering a compound that inhibits the interaction of TRPV4 and the N-terminus of CD98 or administering a compound that inhibits the interaction of the N-terminus of CD98 and an integrin. In one aspect, described herein is a method of treating a disease in a subject, the method comprising administering a compound that inhibits the interaction of TRPV4 and the N-terminus of CD98 to the subject or administering a compound that inhibits the interaction of the N-terminus of CD98 and integrin to the subject. In one aspect, described herein is a method of treating a disease in a subject, the method comprising (a) administering an antagonist of chemically-dependent TRPV4 signaling to the subject; and (b) administering an antagonist of mechanically-dependent TRPV4 signaling to the subject wherein the antagonist of mechanically-dependent TRPV4 signaling is (i) a compound that inhibits the interaction of TRPV4 and the N-terminus of CD98, (ii) a compound that inhibits the interaction of the N-terminus of CD98 and integrin, (iii) a compound that binds the extracellular domain of CD98 and inhibits the interaction of TRPV4 and CD98 or (iv) a compound that modulates integrin signaling. In some embodiments the disease is selected from the group consisting of pulmonary edema; systemic edema; hypertension; hyperalgesia; inflammation; brachyolmia; spondylometaphyseal dysplasia Kozlowski type; metatropic dysplasia; peripheral neuropathy; asthma; COPD; overactive bladder; incontinence; and acoustic cochlear injury. In some embodiments, the compound which is administered is a polypeptide, a nucleic acid, a vector, or a pharmaceutical composition as described herein. In some embodiments, the compound is caused to penetrate a cell via electroporation or magnetoporation.

In one aspect, described herein is a method of identifying an inhibitor of the mechanically-dependent activation of TRPV4, the method comprising contacting a complex comprising TRPV4 and CD98, and optionally, integrin with a candidate agent, measuring the level of complexed TRPV4 and CD98, and optionally, integrin, wherein a decrease in the level of TRPV4 complexed with CD98, or the level of integrin complexed with either TRPV or CD98 indicates the candidate can inhibit the mechanically-dependent activation of TRPV4. In some embodiments, the complex is formed in vitro. In some embodiments, the complex is present in a cell. In some embodiments, the level of TRPV4 complexed with CD98 is determined by measuring the level of TRPV4 present in focal adhesions in a cell. In some embodiments, the focal adhesion is detected by the localization of vinculin.

BRIEF DESCRIPTION OF THE DRAWINGS

FIG. 1A depicts the results of an immunoblot that demonstrates that CD98 and β1-integrin co-precipitate from whole cells using anti-TRPV4 antibody. The amount of each component in the total cell lysates is given in the left panel. In the other two lanes the cell lysates were immuno-precipitated with rabbit IgG as negative control or rabbit anti-TRPV4 antibody. FIG. 1B depicts the results of immu-nblots demonstrating that TRPV4 similarly co-precipitates with either anti-β1-integrin or anti-CD98 antibody. The amount of TRVP4 is given in the left panel. In the other three lanes, the cell lysates were immunoprecipitated with mouse IgG as a negative control or mouse anti-CD98 antibody or mouse anti-β1-integrin.

FIG. 2A depicts a schematic representation of TRPV4. (PR=proline rich domain; AR=ankyrin repeat domain; TM=transmembrane domain) FIG. 2B depicts immunoblot results demonstrating TRPV4 binding to β1-in-tegrin or CD98. Myc vector, myc-linked full-length TRPV4, myc-linked TRPV4 that lacks proline rich domain (ΔPR), or myc-linked TRPV4 lacking all ankyrin repeat domains (ΔAR1-3) was transfected into HEK293T cells 12 h after plating, and the cells were harvested 24 h later. The right panel gives the Western blotting for the expression of each transgene in total cell lysates of respective transfectants. In the left and middle panels, the lysates were immunoprecipi-tated with the anti-β1-integrin or CD98 antibody and the presence or absence of each molecule in the immunopre-cipitates was blotted with anti-myc antibody. FIG. 2C depicts a schematic representation of CD98. (HH=high homology domain from Drosophila to mammal; TM=transmembrane domain). FIG. 2D depicts immunoblot results demonstrating CD98 binding to β1-integrin or TRPV4. HA vector, HA-linked full-length CD98, HA-linked CD98 that lacks high homology domain (ΔHH) was transfected into HEK293T cells as described in FIG. 2B, cell lysates were immunoprecipitated with anti-β1-integrin or TRPV4 antibody, and the presence or absence of each transgene in the precipitates was blotted with anti-HA antibody.

FIG. 6A depicts a graph of the relative change in cytosolic calcium in response to static stretch (20%, 4 second arrow) in Fluo-4-loaded CE cells treated with control or CD98 siRNA. FIG. 6B depicts a graph of the average relative increases in cytosolic calcium induced by mechanical strain in HUVE cells treated with control or CD98 siRNA. FIG. 6C depicts a graph of the relative change in cytosolic calcium in response to 4α-PDD (10 μM) in Fluo-4-loaded CE cells treated with control or CD98 siRNA. FIG. 6D depicts a graph of the average relative increases in cytosolic calcium induced by chemical strain in HUVE cells treated with control or CD98 siRNA.

FIG. 9 depicts the primary sequence alignment of CD98 high homology region. In CD98, amino acids 160-201 represents a high homology region that is conserves from Drosophila to human (SEQ ID NOS 23-26, respectively, in order of appearance). * indicates identity, : indicates high similarity, and . indicates low similarity.

DETAILED DESCRIPTION

Figure 1A:
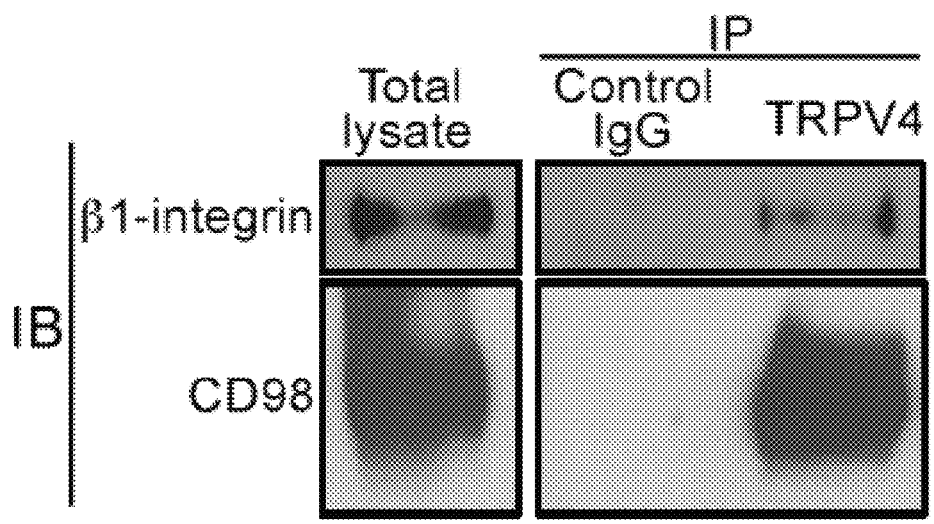
FIGS. 1A-1B demonstrate that β1-integrin, CD98 and TRPV4 co-associate in common signaling complexes inside HUVE cells.

Mechanically-dependent activation of TRPV4 is medi-ated via a complex formed between TRPV4 and CD98 and β1-integrin. As described herein, a particular domain of CD98, termed the "high homology domain," is required for this complex to form, and the subsequent signaling events to occur. Accordingly, compositions and methods to disrupt these TRPV4 complexes and the attendant mechanically-activated signaling, e.g. by inhibiting the ability of the high homology domain of CD98 to interact with TRPV4 and/or β1-integrin, are provided herein.

As described herein, "TRPV4" or "transient receptor potential vanilloid 4" refers to a mechanically- and chemically-sensitive calcium channel of the TRP channel family. The sequence of TRPV4 for a number of species is well known in the art, e.g., human TRPV4 (e.g. NCBI Gene ID: 59341; (mRNA: SEQ ID NO: 2, NCBI Ref Seq: NM_021625)(polypeptide: SEQ ID NO: 3, NCBI Ref Seq: NP_067638). TRPV4 can be activated by chemical and/or mechanical input signals. As described herein, "mechanically-dependent activation of TRPV4" refers to activation of TRPV4 that occurs as a result of mechanical stimulus, e.g. shear stress, pressure, tension, compression or mechanical strain. Markers of mechanically-dependent TRPV4 activation, and methods of detecting them are known in the art (see, e.g Thodeti et al. Circulation Research 2009 104:1123-1130; which is incorporated by reference herein in its entirety), and include, but are not limited to calcium influx, PI3K activation, integrin recruitment, and cytoskeletal remodeling. As described herein, "chemically-dependent activation of TRPV4" refers to activation of TRPV4 that occurs as a result of chemical stimulus, e.g. the binding of a ligand that stimulates channel opening and activity. TRPV4 activation can be determined, e.g. by measuring the influx of calcium into a cell comprising a TRPV4 channel by methods well known in the art.

As used herein, the term "inhibitor" (e.g. inhibitor of TRPV4 activation or of interaction of CD98 and TRPV4 and/or an integrin) refers to an agent which can decrease the targeted activity and/or interaction, e.g. by at least 10% or more, e.g. by 10% or more, 50% or more, 70% or more, 80% or more, 90% or more, 95% or more, or 98% or more. Non-limiting examples of inhibitors of the chemically-dependent activation of TRPV4 can include GSK2193874, HC-067047, GSK205, ruthenium red, RN-1734, RN-9893, capsazepine, citral, and the inhibitors described in, e.g. International Patent Publications WO2009/111680, WO2009/146177, WO2009/146182, WO2010/011912, WO2010/011914, and Japanese Patent Publication JP 2009-084209.

As described herein, "integrin" refers to a class of transmembrane receptors that mediate the attachment of a cell to surrounding materials, e.g. extracellular matrix (ECM) or other cells, as well as transduce signals relating to the chemical and mechanical status of the surrounding materials and/or transduce signals from the cell to the surrounding materials. Integrins function as heterodimers, comprising an alpha chain and a beta chain. Mammalian genomes contain eighteen alpha subunits and eight beta subunits. In some embodiments of any of the aspects described herein, an integrin can be a β1-integrin. As described herein, "β1-integrin" refers to a complete integrin heterodimer comprising a β1 beta chain and any of the eighteen possible alpha chains (e.g. α1-α11, αD, αE, αL, αM, αV, αX or α2B). The sequence of the β1 beta chain (i.e. ITGB1) for a number of species is well known in the art, e.g., human ITGB1 (e.g. NCBI Gene ID: 3688; (mRNA: SEQ ID NO: 4, NCBI Ref Seq: NM_002211)(polypeptide: SEQ ID NO: 5, NCBI Ref Seq: NP_002202).

As described herein, "CD98," "cluster of differentiation 98," or "LAT1" refers to a heterodimeric membrane transport protein composed of SLC3A2 and SLC7A5 which transports certain amino acids across the plasma membrane (preferentially valine, leucine, isoleucine, tryptophan, and tyrosine). The sequence of SLC3A2 and SLC7A5 for a number of species is well known in the art, e.g., human SLC3A2 (e.g. NCBI Gene ID: 6520; (mRNA: SEQ ID NO: 6, NCBI Ref Seq: NM_001012662)(polypeptide:SEQ ID NO: 7, NCBI Ref Seq: NP_001012680) and human SLC7A5 (e.g. NCBI Gene ID: 8140; (mRNA: SEQ ID NO: 8, NCBI Ref Seq: NM_003486)(polypeptide: SEQ ID NO: 9, NCBI Ref Seq: NP 003477). As described herein, the "high homology domain" of CD98 refers to the domain of CD98 having the sequence of SEQ ID NO: 1, and/or a domain of CD98 having at least 90%, at least 95%, at least 98% or greater homology with the sequence of SEQ ID NO: 1.

In one aspect, described herein is an isolated polypeptide comprising the sequence of SEQ ID NO: 1. In some embodiments, described herein is an isolated polypeptide consisting of the sequence of SEQ ID NO: 1. In some embodiments, the isolated polypeptide comprises no more than 300 amino acids. In some embodiments, the isolated polypeptide comprises no more than 200 amino acids. In some embodiments, the isolated polypeptide comprises no more than 150 amino acids. In some embodiments, the isolated polypeptide comprises no more than 100 amino acids. In some embodiments, the isolated polypeptide comprises no more than 75 amino acids. The foregoing polypeptides are not naturally-occurring polypeptides, e.g. SEQ ID NO: 1 naturally occurs in nature only within the context of the mature CD98 sequence, as opposed to the engineered and/or isolated polypeptides described in this paragraph and elsewhere herein. Significantly, these engineered and/or isolated polypeptides (e.g. a polypeptide comprising the sequence of SEQ ID NO: 1 and comprising no more than 300 amino acids) are demonstrated to possess properties not possessed by the naturally-occurring mature CD98 polypeptide. By way of non-limiting example, the engineered and/or isolated polypeptide can inhibit TRPV4 activation.

An isolated polypeptide as described herein can comprise SEQ ID NO: 1 or a homolog, derivative, variant, conservative substitution variant, deletion mutant, insertion mutant and/or functional fragment thereof. As used herein, a "functional fragment" of, e.g. SEQ ID NO: 1 is a fragment or segment of that polypeptide which can inhibit the binding of TRPV4 and/or integrin to CD98 at least 10% as strongly as the reference polypeptide (i.e. SEQ ID NO: 1), e.g. at least 10%, at least 20%, at least 30%, at least 40%, at least 50%, at least 75%, at least 90%, at least 100% as strongly, or more strongly. Assays for protein-protein binding are well known in the art and include, by way of non-limiting example, immunoprecipitation or colocalization using at least two antibodies, one specific for each binding partner. A functional fragment can comprise conservative substitutions of the sequences disclosed herein.

Variants of the isolated peptides described herein (e.g. SEQ ID NO: 1) can be obtained by mutations of native nucleotide or amino acid sequences, for example SEQ ID NO: 1 or a nucleotide sequence encoding a peptide comprising SEQ ID NO: 1. A "variant," as referred to herein, is a polypeptide substantially homologous to the CD98 high homology domain described herein (e.g. SEQ ID NO: 1), but which has an amino acid sequence different from the sequence described herein because of one or a plurality of deletions, insertions or substitutions.

A homolog of an isolated polypeptide as described herein can also comprise amino acid sequences that are homologous to the regions of CD98 comprised by the isolated polypeptide described herein.

The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, identical to the sequence from which it is derived (referred to herein as an "original" sequence). The degree of homology (percent identity) between an original and a mutant sequence can be determined, for example, by comparing the two sequences using freely available computer programs commonly employed for this purpose on the world wide web. The variant amino acid or DNA sequence preferably is at least 60%, at least 70%, at least 80%, at least 90%, at least 91%, at least 92%, at least 93%, at least 94%, at least 95%, at least 96%, at least 97%, at least 98%, at least 99%, or more, similar to the sequence from which it is derived (referred to herein as an "original" sequence). The degree of similarity (percent similarity) between an original and a mutant sequence can be determined, for example, by using a similarity matrix. Similarity matrices are well known in the art and a number of tools for comparing two sequences using similarity matrices are freely available online, e.g. BLASTp (available on the world wide web at blast.ncbi.nlm.nih.gov).

Alterations of the original amino acid sequence can be accomplished by any of a number of known techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations include those disclosed by Walder et al. (Gene 42:133, 1986); Bauer et al. (Gene 37:73, 1985); Craik (BioTechniques, January 1985, 12-19); Smith et al. (Genetic Engineering: Principles and Methods, Plenum Press, 1981); and U.S. Pat. Nos. 4,518,584 and 4,737,462, which are herein incorporated by reference in their entireties. In some embodiments, an isolated peptide as described herein can be chemically synthesized and mutations can be incorporated as part of the chemical synthesis process.

Variants can comprise conservatively substituted sequences, meaning that one or more amino acid residues of an original peptide are replaced by different residues, and that the conservatively substituted peptide retains a desired biological activity, i.e., the ability to inhibit the binding of CD98 to TRPV4 and/or an integrin, that is essentially equivalent to that of the original peptide. Examples of conservative substitutions include substitutions that do not change the overall or local hydrophobic character, substitutions that do not change the overall or local charge, substitutions by residues of equivalent sidechain size, or substitutions by sidechains with similar reactive groups.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics or substitutions of residues with similar sidechain volume are well known. Isolated peptides comprising conservative amino acid substitutions can be tested in any one of the assays described herein to confirm that a desired activity, e.g. the ability to inhibit the binding of CD98 to TRPV4 and/or an integrin, is retained, as determined by the assays described elsewhere herein.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile, Phe, Trp; (2) neutral hydrophilic: Cys, Ser, Thr, Asn, Gln, Ala, Tyr, His, Pro, Gly; (3) acidic: Asp, Glu; (4) basic: His, Lys, Arg; (5) residues that influence chain orientation: Gly, Pro; (6) aromatic: Trp, Tyr, Phe, Pro, His, or hydroxyproline. Non-conservative substitutions will entail exchanging a member of one of these classes for another class.

Particularly preferred conservative substitutions for use in the variants described herein are as follows: Ala into Gly or into Ser; Arg into Lys; Asn into Gln or into His; Asp into Glu or into Asn; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr or into Phe; Tyr into Phe or into Trp; and/or Phe into Val, into Tyr, into Ile or into Leu. In general, conservative substitutions encompass residue exchanges with those of similar physicochemical properties (i.e. substitution of a hydrophobic residue for another hydrophobic amino acid).

Any cysteine residue not involved in maintaining the proper conformation of the isolated peptide as described herein can also be substituted, generally with serine, to improve the oxidative stability of the molecule and prevent aberrant crosslinking. Conversely, cysteine bond(s) can be added to the isolated peptide as described herein to improve its stability or facilitate multimerization.

In some embodiments, the isolated polypeptide further comprises a cell-penetrating agent. As used herein, "cell-penetrating agent" refers to an agent, e.g. an amino acid sequence, capable of crossing the lipid bilayer of a cell. Several cell penetrating peptides have been identified which can be used as cell-penetrating agents for transporting an isolated polypeptide as described herein across cell membranes. These peptides include, but are not limited to, the homeodomain of antennapedia, a Drosophila transcription factor (Wang et al., (1995) PNAS USA., 92, 3318-3322); a fragment representing the hydrophobic region of the signal sequence of Kaposi fibroblast growth factor with or without NLS domain (Antopolsky et al. (1999) Bioconj. Chem., 10, 598-606); a signal peptide sequence of caiman crocodylus Ig(5) light chain (Chaloin et al. (1997) Biochem. Biophys. Res. Comm., 243, 601-608); a fusion sequence of HIV envelope glycoprotein gp4114, (Morris et al. (1997) Nucleic Acids Res., 25, 2730-2736); a transportan A-achimeric 27-mer consisting of N-terminal fragment of neuropeptide galanine and membrane interacting wasp venom peptide mastoporan (Lindgren et al., (2000), Bioconjugate Chem., 11, 619-626); a peptide derived from influenza virus hemagglutinin envelop glycoprotein (Bongartz et al., 1994, Nucleic Acids Res., 22, 468 1 4688); RGD peptide; HIV-1 TAT protein (Frankel and Pabo, (1988) Cell, 55, pp. 1189-93). See also, e.g., Morris, M. C. et al., Nature Biotechnol. 19:1173-1176 (2001); Dupont, A. J. and Prochiantz, A., CRC Handbook on Cell Penetrating Peptides, Langel, Editor, CRC Press, (2002); Chaloin, L. et al., Biochemistry 36(37):11179-87 (1997); and Lundberg, P. and Langel, U., J. Mol. Recognit. 16(5):227-233 (2003); each of which is incorporated herein by reference in its entirety. In some embodiments, the cell-penetrating agent is selected from the group consisting of TAT polypeptide or a lipid protein delivery reagent, e.g, BIOPORTER™. Non-limiting example cell penetration peptide sequences are set forth in Table 1.

TABLE 1

| PEPTIDE | SEQUENCE | SEQ ID NO: |
|---|---|---|
| HIV-1 TAT (49-57) | RKKRRQRRR | SEQ ID NO: 10 |
| HIV-1 TAT (48-60) | GRKKRRQRRRTPQ | SEQ ID NO: 11 |
| HIV-1 TAT (47-57) | YGRKKRRQRRR | SEQ ID NO: 12 |
| Kaposi fibroblast growth factor | AAV ALL PAV LLA LLA P + VQR KRQ KLMP | SEQ ID NO: 13 |
| Signal peptide sequence of caiman crocodylus Ig(5) light chain | MGL GLH LLV LAA ALQ GA | SEQ ID NO: 14 |
| HIV envelope glycoprotein gp41 | GAL FLG FLG AAG STM GA + PKS KRK 5 (NLS of the SV40) | SEQ ID NO: 15 |
| Drosophila Antennapedia | RQI KIW FQN RRM KWK K amide | SEQ ID NO: 16 |
| influenza virus hemagglutinin envelop glycoprotein | GLFEAIAGFIENGWEGMIDGGG YC | SEQ ID NO: 17 |
| transportan A | GWT LNS AGY LLG KIN LKA LAA LAK KIL | SEQ ID NO: 18 |
| Pre-S-peptide | (S)DH QLN PAF | SEQ ID NO: 19 |
| Somatostatin (tyr-3-octreotate) | (S)FC YWK TCT | SEQ ID NO: 20 |

(s) optional Serine for coupling
italic = optional D isomer for stability

In another embodiment, the cell penetrating agent can comprise a membrane signal peptide or membrane translocation sequence capable of translocating across the cell membrane. A cell penetrating "signal peptide" or "signal sequence" refers to a sequence of amino acids generally of a length of about 10 to about 50 or more amino acid residues, many (typically about 55-60%) residues of which are hydrophobic such that they have a hydrophobic, lipid-soluble portion. Generally, a signal peptide is a peptide capable of penetrating through the cell membrane to allow the import and/or export of cellular proteins. Signal peptides can be selected from the SIGPEP database (von Heijne, Protein Sequence Data Analysis 1:4142 (1987); von Heijne and Abrahmsen, L., FEBS Letters 224:439-446 (1989)). Algorithms can also predict signal peptide sequences for use in the compositions (see, e.g., SIGFIND—Signal Peptide Prediction Server version SignalP V2.0b2, Bendtsen et al. "Improved prediction of signal peptides: SignalP 3.0."J. Mol. Biol., 340:783-795, 2004; Nielsen et al. "Identification of prokaryotic and eukaryotic signal peptides and prediction of their cleavage sites." Protein Engineering, 10:1-6, 1997; Bairoch and Boeckmann, "The SWISS-PROT protein sequence data bank: current status" Nucleic Acids Res. 22:3578-3580, 1994).

In some embodiments of the present invention, the isolated polypeptide comprises a cell-penetrating agent. In some embodiments, the isolated polypeptide can be conjugated to a cell-penetrating agent, e.g. the cell-penetrating agent is not present as fusion protein with, e.g. SEQ ID NO: 1. For example, the isolated polypeptide may have a cell penetrating peptide conjugated the polypeptide by chemical bond linkages, such as linkages by disulfide bonds or by chemical bridges. Peptide sequences of the present invention can also be linked together using non-peptide cross-linkers (Pierce 2003-2004 Applications Handbook and Catalog, Chapter 6) or other scaffolds such as HPMA, polydextran, polysaccharides, ethylene-glycol, poly-ethylene-glycol, glycerol, sugars, and sugar alcohols (e.g., sorbitol, mannitol).

In one aspect, described herein, is an isolated nucleic acid encoding an isolated polypeptide described herein. In one aspect, described herein, is a vector comprising an isolated nucleic acid encoding an isolated polypeptide described herein.

Nucleic acid molecules encoding an isolated polypeptide as described herein are prepared by a variety of methods known in the art. These methods include, but are not limited to, PCR, ligation, and direct synthesis. A nucleic acid sequence encoding a polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., Molecular Cloning, Lab. Manual (Cold Spring Harbor Lab. Press, NY, 1982 and 1989), and Ausubel, 1987, 1993, and can be used to construct nucleic acid sequences which encode an isolated polypeptide as described herein.

The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

In one aspect, the technology described herein relates to an expression vector comprising a nucleic acid encoding any of the isolated polypeptides described herein. Such vectors can be used, e.g. to transform a cell in order to produce the encoded polypeptide. As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in mammalian cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. Vectors useful for the delivery of a sequence encoding an isolated peptide as described herein can include one or more regulatory elements (e.g., promoter, enhancer, etc.) sufficient for expression of the isolated peptide in the desired cell or tissue. The regulatory elements can be chosen to provide either constitutive or regulated/inducible expression. As used herein, the term "viral vector" refers to a nucleic acid vector construct that includes at least one element of viral origin and has the capacity to be packaged into a viral vector particle. The viral vector can contain the nucleic acid encoding an antibody or antigen-binding portion thereof as described herein in place of non-essential viral genes. The vector and/or particle may be utilized for the purpose of transferring any nucleic acids into cells either in vitro or in vivo. Numerous forms of viral vectors are known in the art.

Examples of vectors useful in delivery of nucleic acids encoding isolated peptides as described herein include plasmid vectors, non-viral plasmid vectors (e.g. see U.S. Pat. Nos. 6,413,942, 6,214,804, 5,580,859, 5,589,466, 5,763,270 and 5,693,622, all of which are incorporated herein by reference in their entireties); retroviruses (e.g. see U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Miller et al., Meth. Enzymol. 217:581-599 (1993); Burns et al. (1993) Proc. Natl. Acad. Sci. USA 90:8033-37; Boris-Lawrie and Temin (1993) Curr. Opin. Genet. Develop. 3:102-09. Boesen et al., Biotherapy 6:291-302 (1994); Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993), the contents of each of which are herein incorporated by reference in their entireties); lentiviruses (e.g., see U.S. Pat. Nos. 6,143,520; 5,665,557; and 5,981,276, the contents of which are herein incorporated by reference in their entireties); adenovirus-based expression vectors (e.g., see Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) Bio-Techniques 6:616-29; and Rich et al. (1993) Human Gene Therapy 4:461-76; Wu et al. (2001) Anesthes. 94:1119-32; Parks (2000) Clin. Genet. 58:1-11; Tsai et al. (2000) Curr. Opin. Mol. Ther. 2:515-23; and U.S. Pat. Nos. 6,048,551; 6,306,652 and 6,306,652, incorporated herein by reference in their entireties); Adeno-associated viruses (AAV) (e.g. see U.S. Pat. Nos. 5,139,941; 5,622,856; 5,139,941; 6,001,650; and 6,004,797, the contents of each of which are incorporated by reference herein in their entireties); and avipox vectors (e.g. see WO 91/12882; WO 89/03429; and WO 92/03545; which are incorporated by reference herein in their entireties).

Useful methods of transfection can include, but are not limited to electroporation, sonoporation, protoplast fusion, peptoid delivery, or microinjection. See, e.g., Sambrook et al (1989) Molecular Cloning, A Laboratory Manual, Cold Spring Harbor Laboratories, New York, for a discussion of techniques for transforming cells of interest; and Felgner, P. L. (1990) Advanced Drug Delivery Reviews 5:163-87, for a review of delivery systems useful for gene transfer. Exemplary methods of delivering DNA using electroporation are described in U.S. Pat. Nos. 6,132,419; 6,451,002, 6,418,341, 6,233,483, U.S. Patent Publication No. 2002/0146831, and International Publication No. WO/0045823, all of which are incorporated herein by reference in their entireties.

In some embodiments, the nucleic acid encoding an isolated polypeptide as described herein can be operatively linked to, e.g. a promoter or other transcriptional regulatory sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence. In some examples, transcription of a nucleic acid modulatory compound is under the control of a promoter sequence (or other transcriptional regulatory sequence) which controls the expression of the nucleic acid in a cell-type in which expression is intended. It will also be understood that the modulatory nucleic acid can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

In some embodiments, the vector comprising a nucleic acid encoding an isolated polypeptide as described herein and/or a nucleic acid encoding an isolated polypeptide as described herein, can be present in a cell. The cell can be, e.g. a microbial cell or a mammalian cell. In some embodiments, the cell as described herein is cultured under conditions suitable for the expression of the isolated polypeptide described herein. Such conditions can include, but are not limited to, conditions under which the cell is capable of growth and/or polypeptide synthesis. Conditions may vary depending upon the species and strain of cell selected. Conditions for the culture of cells, e.g. prokaryotic and mammalian cells, are well known in the art. If the recombinant polypeptide is operatively linked to an inducible promoter, such conditions can include the presence of the suitable inducing molecule(s).

In one aspect, described herein is a pharmaceutical composition comprising an isolated polypeptide described herein, a nucleic acid encoding an isolated polypeptide as described herein, and/or a vector comprising a nucleic acid encoding an isolated polypeptide as described herein and a pharmaceutically acceptable carrier.

TRPV4 activity has been implicated in, e.g. breathing motions, ECM strain, fluid shear stress, pulmonary vascular pressure, barotraumas, serum osmolarity control, nociception, thermal sensing, CNS regulation, bone formation and remodeling, bladder tone, motor and sensory neuritogenesis, inflammation, adipocyte homeostasis, vascular permeability and drug delivery. Modulation of TRPV4 therefore has a number of applications, both therapeutically and as a research tool. In one aspect, provided herein is a method of inhibiting the mechanically-dependent activation of TRPV4, the method comprising administering a compound that inhibits the interaction of TRPV4 and the N-terminus of CD98 or administering a compound that inhibits the interaction of the N-terminus of CD98 and an integrin. The activation of TRPV4 can be measured in accordance with methods known to one of ordinary skill in the art, e.g. by measuring in the influx of calcium into the cell, e.g. in the presence of a known stimulus of TRPV4 (e.g. either mechanical or chemical). Methods of measuring calcium flux are well known in the art, e.g. by measuring the fluorescence of a calcium reporter dye such as Fluo-4 (see, e.g Thodeti et al. Circulation Research 2009 104:1123-1130; which is incorporated by reference herein in its entirety)

In one aspect, described herein is a method of treating a disease in a subject, the method comprising administering a compound that inhibits the interaction of TRPV4 and the N-terminus of CD98 to the subject or administering a compound that inhibits the interaction of the N-terminus of CD98 and integrin to the subject. Non-limiting examples of diseases that can be treated in accordance with the methods described herein include pulmonary edema, systemic edema, hypertension, hyperalgesia, inflammation, brachyolmia, spondylometaphyseal dysplasia Kozlowski type, metatropic dysplasia, peripheral neuropathy, asthma, COPD, overactive bladder, incontinence, and acoustic cochlear injury. Diseases which are caused, at least in part, by abnormally high levels of TRPV4 signaling are known in the art. See, e.g. Nilius et al. Physiological Reviews 2007 87:165-217; which is incorporated by reference herein in its entirety.

The compound that inhibits the interaction of TRPV4 and the N-terminus of CD98 and/or inhibits the interaction of the N-terminus of CD98 and an integrin can be, e.g. an isolated polypeptide as described herein, a nucleic acid encoding an isolated polypeptide as described herein, a vector comprising a nucleic acid encoding an isolated polypeptide as described herein, or a pharmaceutical composition comprising one or more of the preceding agents. In some embodiments, the compound can be caused to penetrate a cell via electroporation or magnetoporation.

As the compounds described herein permit specific inhibition of mechanically-dependent TRPV4 signaling, without impacting chemically-dependent TRPV4 signaling, the combination of an inhibitor of mechanically-dependent TRPV4 signaling and an inhibitor of chemically-dependent TRPV4 signaling can be additive and/or synergistic in inhibiting total TRPV4 signaling activity. Accordingly, provided herein is a method of treating a disease in a subject, the method comprising administering an antagonist of chemically-dependent TRPV4 signaling to the subject and administering an antagonist of mechanically-dependent TRPV4 signaling to the subject. Inhibitors (e.g. antagonists) of chemically-dependent TRPV4 signaling are described elsewhere herein. In some embodiments, the antagonist of mechanically-dependent TRPV4 signaling can be (i) a compound that inhibits the interaction of TRPV4 and the N-terminus of CD98, (ii) a compound that inhibits the interaction of the N-terminus of CD98 and an integrin, (iii) a compound that binds the external domain of CD98 and inhibits the interaction of TRPV4 and CD98, and/or (iv) a compound that modulates integrin signaling.

As used herein, a compound that binds the extracellular domain of CD98 (e.g. amino acids 207-631 of SEQ ID NO: 7 and/or amino acids 76-84, 157-170, 221-239, 297-321, 419-432, and/or 479-507 of SEQ ID NO: 9) and inhibits the interaction of TRPV4 and CD98 can be, e.g. an antibody, antibody reagent, peptide, or aptamer. Methods of determining if a compound binds the extracellular domain of CD98, as well as methods for detecting the interaction of CD98 and TRPV4 are well known in the art, e.g. by immunoprecipitation or immunochemistry, and/or by using labeled reagents and are described elsewhere herein.

As used herein, a compound that inhibits integrin signaling can be a compound that decreases the amount of one or more integrins and/or inhibits integrin activation. A compound that decreases the amount of one or more integrins, can be, e.g. an inhibitory RNAi that targets one or more integrin subunits. A compound that inhibits integrin activation can be, e.g. an agent that binds to integrin, preventing phosphorylation, e.g. an antibody reagent that blocks integrin activation. Such reagents are known in the art and are commercially available, e.g. function-blocking anti-β1-integrin (P5D2) available as Cat No. sc-13590 (Santa Cruz Biotech, Dallas, Tex.).

In some embodiments, the methods described herein relate to treating a subject having or diagnosed as having a condition described herein, e.g. pulmonary edema, with a method or composition described herein. Subjects having, e.g. pulmonary edema can be identified by a physician using current methods of diagnosing pulmonary edema. Symptoms and/or complications of pulmonary edema which characterize these conditions and aid in diagnosis are well known in the art and include but are not limited to, difficulty breathing, coughing up blood, excessive sweating, anxiety, pale skin, shortness of breath, edema, elevated jugular venous pressure, and hepatomegaly. Tests that may aid in a diagnosis of, e.g. pulmonary edema include, but are not limited to, tests for oxygen saturation in the blood, chest x-ray, echocardiography, blood tests for electrolytes and renal function, blood count, coagulation test, and tests for levels of B-type natriuretic peptide (BNP). A family history of pulmonary edema, or exposure to risk factors for pulmonary edema (e.g. heart attack, kidney failure, hypertensive crisis, seizures, head trauma, or electrocution) can also aid in determining if a subject is likely to have pulmonary edema or in making a diagnosis of pulmonary edema.

The compositions and methods described herein can be administered to a subject having or diagnosed as having a condition described herein, e.g. pulmonary edema In some embodiments, the methods described herein comprise administering an effective amount of compositions described herein, e.g. an isolated polypeptide described herein, to a subject in order to alleviate a symptom of, e.g. pulmonary edema. As used herein, "alleviating a symptom of" a condition is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection or topical administration. Administration can be local or systemic.

The term "effective amount" as used herein refers to the amount of a composition (e.g. an isolated polypeptide as described herein) needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for fluid leakage in an in vitro model of pulmonary edema as described elsewhere herein, among others. The dosage can be determined by a physician and adjusted, as necessary, to suit observed effects of the treatment.

In some embodiments, the technology described herein relates to a pharmaceutical composition comprising, e.g. an isolated polypeptide as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent.

In some embodiments, the pharmaceutical composition can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. By way of non-limiting example, if a subject is to be treated for pain or inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g. endorphins, enkephalins, and dynorphin), steroids, analgesics, barbiturates, oxycodone, morphine, lidocaine, and the like.

In certain embodiments, an effective dose of a composition comprising, e.g. an isolated polypeptide as described herein can be administered to a patient once. In certain embodiments, an effective dose of a composition can be administered to a patient repeatedly. For systemic administration, subjects can be administered a therapeutic amount of a composition, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. edema in a subject with pulmonary edema by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of the compositions described herein, according to the methods described herein depend upon, for example, the form of the composition, its potency, and the extent to which symptoms, markers, or indicators of a condition described herein are desired to be reduced, for example the percentage reduction desired for edema, pain, or inflammation. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein (e.g. modulation of TRPV4 activity) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. BNP levels in a subject with pulmonary edema. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of pulmonary edema. When using an experimental animal model, efficacy of treatment is evidenced when a statistically significant change in a marker is observed.

In vitro and animal model assays are provided herein which allow the assessment of a given dose of a composition described herein. By way of non-limiting example, the effects of a dose of an isolated polypeptide described herein can be assessed by an in vitro model of pulmonary edema as described in, e.g. Hamilton et al. Sci Transl Med 2012 4:159; which is incorporated by reference herein in its entirety. A non-limiting example of a protocol for such an assay is as follows: IL-2 (1000 U/ml) is perfused through an in vitro model of lung tissue (e.g. lung-on-chip, as described in Hamilton et al. and International Patent Publication PCT/US2009/050830; each of which is incorporated by reference herein in its entirety). Fluid leakage from the cells can be measured by, e.g. phast contrast microscopy to determine the accumulation of fluid in the air-filled alveolar compartment. The level of fluid leakage can be quantified, e.g. by injecting fluorescein isothiocynate (FITC)-conjugated inulin into the microvascular compartment and measuring the fluorescence in fluid subsequently collected in the alveolar compartment.

In one aspect, provided herein is a method of identifying an inhibitor of the mechanically-dependent activation of TRPV4, the method comprising contacting a complex comprising TRPV4 and CD98, and optionally, integrin with a candidate agent, measuring the level of complexed TRPV4 and CD98, and optionally, integrin; wherein a decrease in the level of TRPV4 complexed with CD98, or the level of integrin complexed with either TRPV4 or CD98 in the presence of the candidate agent indicates the candidate can inhibit the mechanically-dependent activation of TRPV4. In some embodiments, the level is decreased if it is lower by a statistically significant amount. In some embodiments, the candidate agent that is screened and identified to inhibit TRPV4 mechanically-dependent activation can decrease the level of, e.g. TRPV4 complexed with CD98 by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to an untreated control.

As used, herein, a "complex" refers to two or more polypeptides (e.g. CD98 and an integrin, TRPV4 and CD98, or CD98, TRPV4, and an integrin) which are bound together. A complex can form when the two or more polypeptides are present in the same solution and/or cell under suitable conditions, e.g. physiologic pH. In some embodiments, the complex can be formed in vitro, e.g. isolated CD98 and TRPV4 polypeptides, and/or their soluble extracellular domains or intracellular domains, can be expressed separately and then combined under conditions suitable for the formation of a complex in vitro. In some embodiments, the complex can be present in a cell, e.g. the CD98 and TRPV4 can be expressed in the same cell at detectable levels. In some embodiments, one or more of the polypeptides can comprise a detectable label.

In some embodiments the TRPV4, CD98 and/or integrin can be obtained by expressing the polypeptides in a cell, e.g. using a vector as described elsewhere herein. In some embodiments, TRPV4, CD98 and/or integrin are expressed in a eurkaryotic cell. In some embodiments, TRPV4, CD98 and/or integrin are expressed are synthesized in vitro. The polypeptides can be expressed and isolated using methods well known to those of ordinary skill in the art, e.g. as described in Sanbrook et al, Molecular Cloning: A Laboratory Manual ($3^{rd}$ Ed) 2001, CSH Press, Cold Spring Harbor, N.Y. Isolated polypeptides can be obtained by similar methods.

In some embodiments, one or more of the polypeptides or agents (e.g. an antibody reagent) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the polypeptide or agent. Alternatively, a detectable label can be linked such as by directly labeling a molecule that achieves binding to the polypeptide or agent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the label is a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4',7',4,7-hexachlorofluorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^{3}H$, $^{125}I$, $^{35}S$, $^{14}C$, $^{32}P$, and $^{33}P$. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use as a detectable label include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, an agent can be detectable by means of a detectable tag, such as c-Myc, HA, VSV-G, HSV, FLAG, V5, HIS, or biotin. Other detection systems can also be used, for example, a biotin-streptavidin system. In this system, the antibodies immunoreactive (i. e. specific for) with the biomarker of interest is biotinylated. Quantity of biotinylated antibody bound to the biomarker is determined using a streptavidin-peroxidase conjugate and a chromagenic substrate. Such streptavidin peroxidase detection kits are commercially available, e. g. from DAKO; Carpinteria, Calif. A label can also be a fluorescence emitting metal such as $^{152}Eu$, or others of the lanthanide series. These metals can be attached to the polypeptide or agent using such metal chelating groups as diethylenetriaminepentaacetic acid (DTPA) or ethylene diaminetetraacetic acid (EDTA).

In some embodiments, the level of TRPV4 complexed with CD98 is determined by measuring the level of TRPV4 present in focal adhesions in a cell. Methods of determining the concentration and/or presence of a given polypeptide at certain subcellular locations (e.g. focal adhesions) are well known in the art can include, by way of non-limiting example, colocalization of the polypeptide of interest with a molecule known to be present at that location. In some embodiments, a focal adhesion is detected by the localization of vinculin. Antibody reagents for the detection of vinculin are known in the art and are commercially available, e.g. Cat No. V9731 (Sigma-Aldrich; St. Louis, Mo.). Antibodies that can be used to detect each of TRPV4, CD98, and a given integrin (e.g. β1-integrin) are well known in the art and commercially available (e.g., respectively, Cat Nos. ab39260, 3122-1, and 1798-1; Abcam, Cambridge, Mass.).

As used herein, the terms "candidate compound" or "candidate agent" refer to a compound or agent and/or compositions thereof that are to be screened for their ability to modulate binding of CD98 to TRPV4 and/or integrin. In some embodiments, a library of candidate agents can be screened. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule (Woburn, Mass.), Panvera (Madison, Wis.), Ryan Scientific (Mt. Pleasant, S.C.), and Enzo Life Sciences (Plymouth Meeting, Pa.).

Generally, compounds can be tested at any concentration that can inhibit complex formation relative to a control over an appropriate time period. In some embodiments, compounds are tested at concentration in the range of about 0.1 nM to about 1000 mM. In one embodiment, the compound is tested in the range of about 0.1 µM to about 20 µM, about 0.1 µM to about 10 µM, or about 0.1 µM to about 5 µM.

Depending upon the particular embodiment being practiced, the candidate compounds can be provided free in solution, or may be attached to a carrier, or a solid support, e.g., beads. A number of suitable solid supports may be employed for immobilization of the candidate compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylenemaleic acid copolymer, nylon, silk, etc. Additionally, for the methods described herein, candidate compounds may be screened individually, or in groups. Group screening is particularly useful where hit rates for effective candidate compounds are expected to be low such that one would not expect more than one positive result for a given group.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticly significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of disease, e.g. pulmonary edema. A subject can be male or female.

The term "isolated" or "partially purified" as used herein refers to a molecule (e.g. a polypeptide) separated from at least one other component (e.g., a nucleic acid or polypeptide) that is present with the molecule as found in its natural source and/or that would be present with the molecule when expressed by a cell, or secreted in the case of secreted polypeptides. A chemically synthesized nucleic acid or polypeptide or one synthesized using in vitro transcription/translation is considered "isolated."

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon—carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons. In some embodiments, an agent can be an inhibitory nucleic acid; an antibody reagent; an antibody; or a small molecule.

A subject can be one who has been previously diagnosed with or identified as suffering from or having a condition in need of treatment (e.g. pulmonary edema) or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include minibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRS has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody or antibody reagent thereof as described herein. Such functional activities include, e.g. the ability to bind to the extracellular domain of CD98.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

In some embodiments, a binding reagent (e.g. an inhibitor that binds target described herein) can be an aptamer. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (Ellington et al. Nature. 1990; 346(6287):818-822; Tuerk et al., Science. 1990; 249(4968): 505-510; Ni et al., Curr Med Chem. 2011; 18(27):4206-14; which are incorporated by reference herein in their entireties). Methods of generating an apatmer for any given target are well known in the art. Preclinical studies using, e.g. aptamer-siRNA chimeras and aptamer targeted nanoparticle therapeutics have been very successful in mouse models of cancer and HIV (Ni et al., Curr Med Chem. 2011; 18(27): 4206-14).

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part of an mRNA transcript of, e.g. one or more integrins. The use of these iRNAs enables the targeted degradation of mRNA transcripts, resulting in decreased expression and/or activity of the target (e.g. an integrin). The following detailed description discloses how to make and use compositions containing iRNAs to inhibit the expression of a target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of one or more integrins.

In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect, an RNA interference agent relates to a double stranded RNA that promotes the formation of a RISC complex comprising a single strand of RNA that guides the complex for cleavage at the target region of a target transcript to effect silencing of the target gene.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, an miRNA is a dsRNA. In another embodiment, a dsRNA is not a naturally occurring miRNA. In another embodiment, an iRNA agent useful to target expression of a target is not generated in the target cell by cleavage of a larger dsRNA.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6, 239,265; 6,277,603; 6,326, 199; 6,346,614; 6,444,423; 6,531,590; 6,534,639; 6,608, 035; 6,683,167; 6,858,715; 6,867,294; 6,878,805; 7,015, 315; 7,041,816; 7,273,933; 7,321,029; and US Pat RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$, also described in examples herein below.

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acad. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. pulmonary edema. The term "treating" includes reducing or alleviating at least one adverse effect or symptom of a condition, disease or disorder, e.g. pulmonary edema. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An isolated polypeptide comprising the sequence of SEQ ID NO: 1
2. An isolated polypeptide of paragraph 1, further comprising a cell-penetrating agent.
3. The polypeptide of paragraph 2, wherein the cell-penetrating agent is selected from the group consisting of:
   TAT polypeptide or a lipid protein delivery reagent, e.g., BIOPORTER™.
4. An isolated nucleic acid encoding the polypeptide of any of paragraphs 1-3.
5. The nucleic acid of paragraph 4, wherein the nucleic acid is a cDNA.
6. A vector comprising the isolated nucleic acid of any of paragraphs 4-5.
7. A pharmaceutical composition comprising the polypeptide of any of paragraphs 1-3, the nucleic acid of any of paragraphs 4-5, or the vector of paragraph 6 and a pharmaceutically acceptable carrier.
8. A method of inhibiting the mechanically-dependent activation of TRPV4, the method comprising:
   administering a compound that inhibits the interaction of TRPV4 and the N-terminus of CD98; or
   administering a compound that inhibits the interaction of the N-terminus of CD98 and an integrin.
9. A method of treating a disease in a subject, the method comprising:
   administering a compound that inhibits the interaction of TRPV4 and the N-terminus of CD98 to the subject; or
   administering a compound that inhibits the interaction of the N-terminus of CD98 and integrin to the subject.
10. A method of treating a disease in a subject, the method comprising:
    (a) administering an antagonist of chemically-dependent TRPV4 signaling to the subject; and
    (b) administering an antagonist of mechanically-dependent TRPV4 signaling to the subject;
    wherein the antagonist of mechanically-dependent TRPV4 signaling is:
    (i) a compound that inhibits the interaction of TRPV4 and the N-terminus of CD98;
    (ii) a compound that inhibits the interaction of the N-terminus of CD98 and integrin;
    (iii) a compound that binds the extracellular domain of CD98 and inhibits the interaction of TRPV4 and CD98;
    (iv) a compound that modulates integrin signaling.
11. The method of paragraph 10, wherein the disease is selected from the group consisting of:
    pulmonary edema; systemic edema; hypertension; hyperalgesia; inflammation; brachyolmia; spondylometaphyseal dysplasia Kozlowski type; metatropic dysplasia; peripheral neuropathy; asthma; COPD; overactive bladder; incontinence; and acoustic cochlear injury.
12. The method of any of paragraphs 8-11, wherein the compound which is administered is a polypeptide of any of paragraphs 1-3, the nucleic acid of any of paragraphs 4-5, the vector of paragraph 6, or the pharmaceutical composition of paragraph 7.
13. The method of paragraph 12, wherein the compound is caused to penetrate a cell via electroporation or magnetoporation.
14. A method of identifying an inhibitor of the mechanically-dependent activation of TRPV4, the method comprising:
    contacting a complex comprising TRPV4 and CD98, and optionally, integrin with a candidate agent;
    measuring the level of complexed TRPV4 and CD98, and optionally, integrin; wherein a decrease in the level of TRPV4 complexed with CD98, or the level of integrin complexed with either TRPV or CD98 indicates the candidate can inhibit the mechanically-dependent activation of TRPV4.
15. The method of paragraph 14, wherein the complex is formed in vitro.
16. The method of paragraph 14, wherein the complex is present in a cell.
17. The method of paragraph 16, wherein the level of TRPV4 complexed with CD98 is determined by measuring the level of TRPV4 present in focal adhesions in a cell.
18. The method of paragraph 17, wherein the focal adhesion is detected by the localization of vinculin.

EXAMPLES

Example 1

CD98 Mediates Mechanical Signal from β1-Integrin to TRPV4

The conversion of physical force into biochemical information is fundamental to development and physiology. One of the most rapid mechanical events involves integrin-dependent activation of the stress-activated (SA) membrane ion channel Transient receptor potential vanilloid 4 (TRPV4). However, it is still unclear the molecular mechanism by which integrins mediate these "early-immediate" mechanical signaling responses that activate TRPV4. It is reported herein that CD98 mediates mechanical activation of the TRPV4 membrane ion channel by physical forces applied to β1-integrins. As demonstrated herein, TRPV4 associates with β1-integrin and CD98 and localizes at focal adhesion in HUVE cells. Although the formation of focal adhesion occurs, TRPV4 can't localize at focal adhesion in CD98 siRNA-treated cells. Moreover, TRPV4 can't bind to β1-integrin in CD98 siRNA-treated cells. In addition, it is demonstrated herein that actin rearrangement and calcium influx are inhibited in CD98 siRNA-treated cells. Together these findings demonstrate that CD98 plays a role in mechanotransduction by mediating the binding between β1-integrin and TRPV4 at focal adhesion. Additionally, the calcium influx of TRPV4 activation by chemical treatment was not inhibited in CD98 siRNA-treated cells. Without wishing to be bound by theory, the pathway of TRPV4 activation may be different between chemical and mechanical cues.

Introduction

Essentially all organisms from bacteria to humans are mechanosensitive. Cellular mechanotransduction—the mechanism by which cells sense mechanical forces and convert them into changes in cellular biochemistry—is critical for control of the growth and development of all tissues, and deregulation of this process contributes to the etiology of numerous diseases (1). For example, pressure and shear stress from pumping blood influence the morphology and pathology of the heart and vasculature in the vascular system. Bone is shaped by forces from gravity and muscle contraction. Hearing and touch are based on neural responses to pressure. Inflation and deflation of the lungs regulate their physiology. Coordinated growth of tissues is guided by mechanical forces, and failure of these mechanisms contributes to cancer. Therefore, to elucidate the force transmission pathway in the cell body lead to benefits for developing new drugs and treatments for these diseases.

It is reported that mechanotransduction brings about important cellular changes in shape, motility, cytoskeletal remodeling, focal adhesion reorganization and gene expression (2). However, the mechanism by which cells transmit mechanical stress throughout the cytoplasm and the cytoskeleton and how such signals are sensed and converted into biochemical signals is still not understood.

An important group of adhesive transmembrane receptors that mechanically link the Extracellular matrix (ECM) with internal cytoskeleton are integrins. Transmembrane integrin receptors that support ECM adhesion and physically couple ECM to the cytoskeleton mediate mechanotransduction (3). Stress activated (SA) channels represent another class of mechanoreceptors that support the conversion of mechanical force signals applied to the cell surface into transmembrane ion gradients (4). TRPV4 belongs to the Transient Receptor Potential (TRP) superfamily, which consists of at least 33 channel subunit genes divided into 6 sub-families. These proteins are a nonselective calcium-permeable cation channels. They are activated and regulated by a variety of stimuli and are expressed widely. TRPC1, TRPC6, TRPA1, TRPM3, TRPM7 TRPV2 and TRPV4 are reported as mechanosensors among the TRP family (5).

TRPV4 was previously identified as the SA channel responsible for activation of microvascular endothelial cells when mechanical forces are applied to β1-integrin, for example, by mechanically stretching cells attached to ECM-coated flexible substrates (6). However, the molecular mechanism by which integrins mediate these 'early-immediate' mechanical signaling responses that activate TRPV4 are not well understood.

It is possible that the distal most region of the β1-integrin cytoplasmic domain that contains a binding site for transmembrane amino acid transporter CD98 mediates this near instantaneous integrin dependent force induced calcium signal using magnetic pulling cytometry (MPC) and integrin chimera DNA constructions (7). CD98 is known to associate with the β1-integrin cytoplasmic tail (8) and to be required for adhesion strengthening through integrins as well as cytoskeletal tension-dependent fibronectin fibrillogenesis (9). However, the molecular mechanism whereby CD98 could play a role in the molecular connection between these proteins is unclear. Described herein is data indicating that CD98 mediates mechanical activation of the TRPV4 membrane ion channel by physical forces applied to β1-integrins. CD98 binds to both β1-integrin and TRPV4, and is required for mechanical, but not chemical, activation of TRPV4.

Results

Figure 1B:
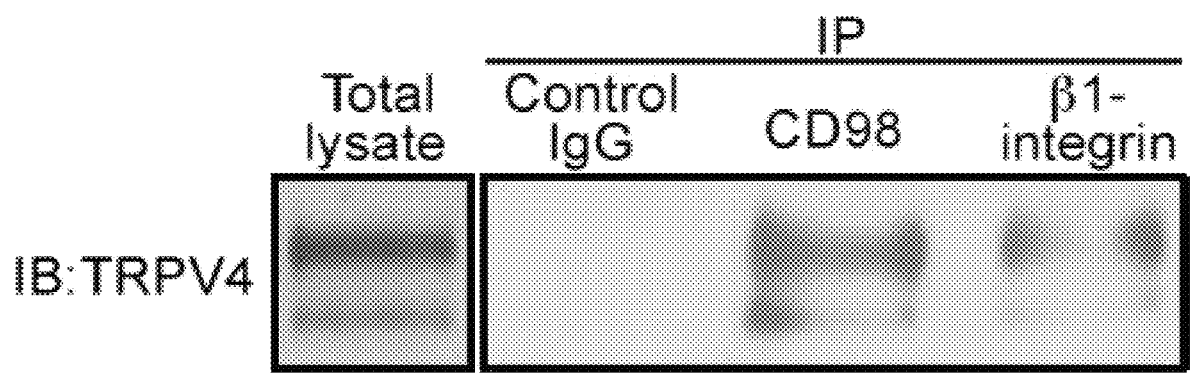

TRPV4 associates with CD98 and β1-integrin at focal adhesion. The terminal 6 amino acid residues at the carboxy end of the β1-integrin cytoplasmic mediate calcium signaling and are required for rapid force induced TRPV4-mediated calcium signaling (10). It was postulated that CD98, which binds to the last 6 carboxy terminal amino acids of β1-integrin, is involved in the TRPV4 activation by β1-integrin using genetically engineered mutant integrin constructs. First, it was confirmed that CD98 binds to integrins through the region of the β1-integrin tail using β1-integrin mutant constructs to transfect HEK293T cells followed by an immunoprecipitation assay. It was also confirmed that TRPV4 also interacts with the same region of β1-integrin using the same β1-integrin mutant constructs (data not shown). To explore the binding between those molecules, whether CD98 and β1-integrin can be co-precipitated from HUVE cell lysates using anti-TRPV4 antibody was determined (FIG. 1A). TRPV4 similarly precipitates with either anti-β1-integrin or anti-CD98 antibody (FIG. 1B). Moreover, it was confirmed that TRPV4 overlapped with CD98 at vinculin positive focal adhesions by Total Internal Reflection Fluorescence (TIRF, data not shown). These findings suggest that these three molecules are structurally linked inside the focal adhesion at the cell's ECM binding site.

Figure 2A:
FIGS. 2A-2D demonstrate that Ankyrin rich domain of TRPV4 and High homology domain of CD98 are important for their binding.
Figure 2B:
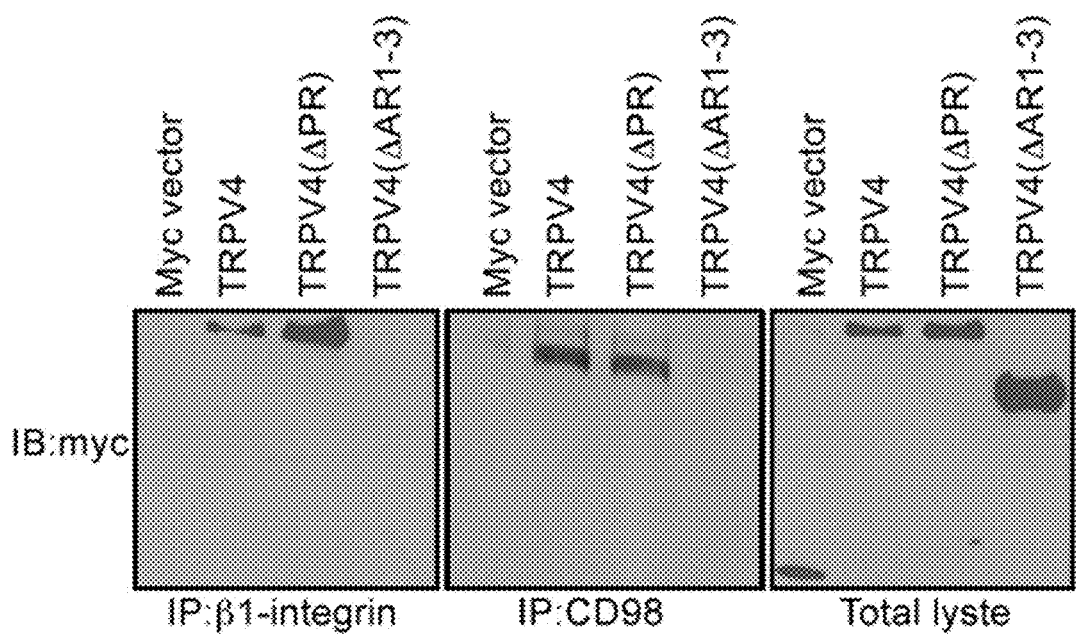

The deletion of the transmembrane region and C-terminal region of TRPV4 did not affect the binding to either β1-integrin or CD98 (data not shown). TRPV4 has one proline rich domain and three ankyrin repeat domains in its N-terminal region (FIG. 2A). Although TRPV4 lacking one proline rich domain could associate with CD98 and β1-integrin, TRPV4 lacking all three ankyrin repeat domains could not (FIG. 2B). This data indicates that TRPV4 associates with β1-integrin and CD98 through its ankyrin repeat regions.

Figure 2C:
Figure 2D:
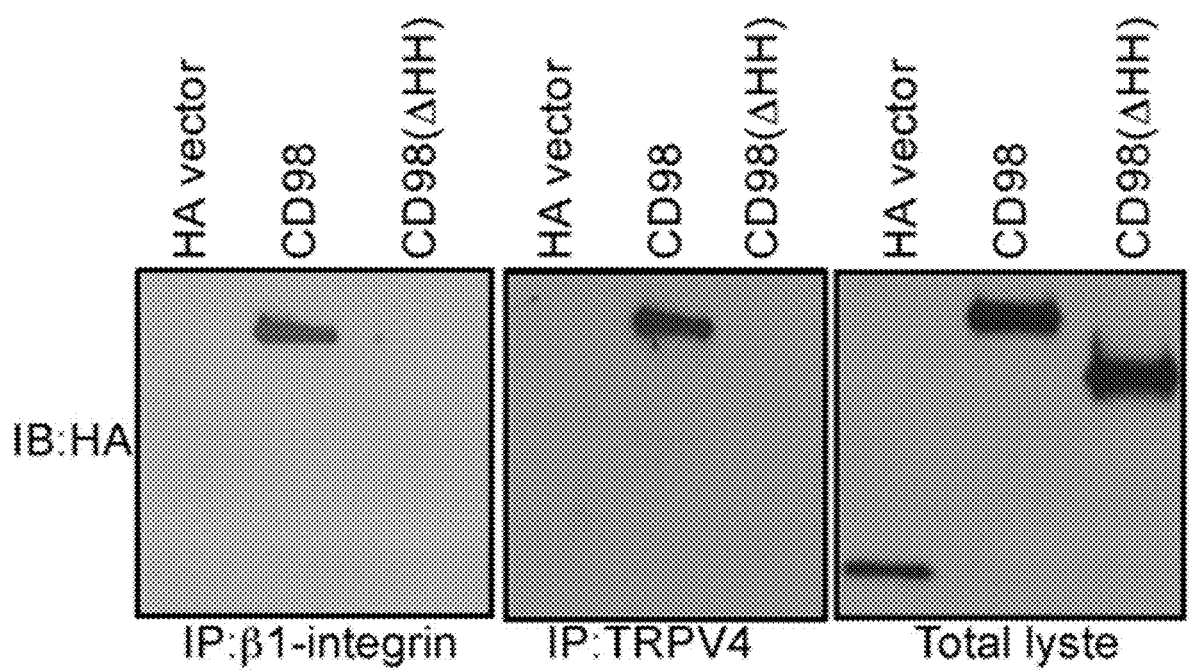

And also, the deletion of the C-terminal region of CD98 did no affect the binding to either β1-integrin or TRPV4 (data not shown). In the N-terminal region of CD98, there is a region which was highly conserved from Drosophila to mammals (FIGS. 2C and 9). The deletion of this domain removed the ability of CD98 to associate with either β1-integrin or TRPV4 (FIG. 2D). Thus, TRPV4, CD98 and β1-integrin make a complex through ankyrin repeat domain of TRPV4 and high homology domain of CD98.

Figure 3:
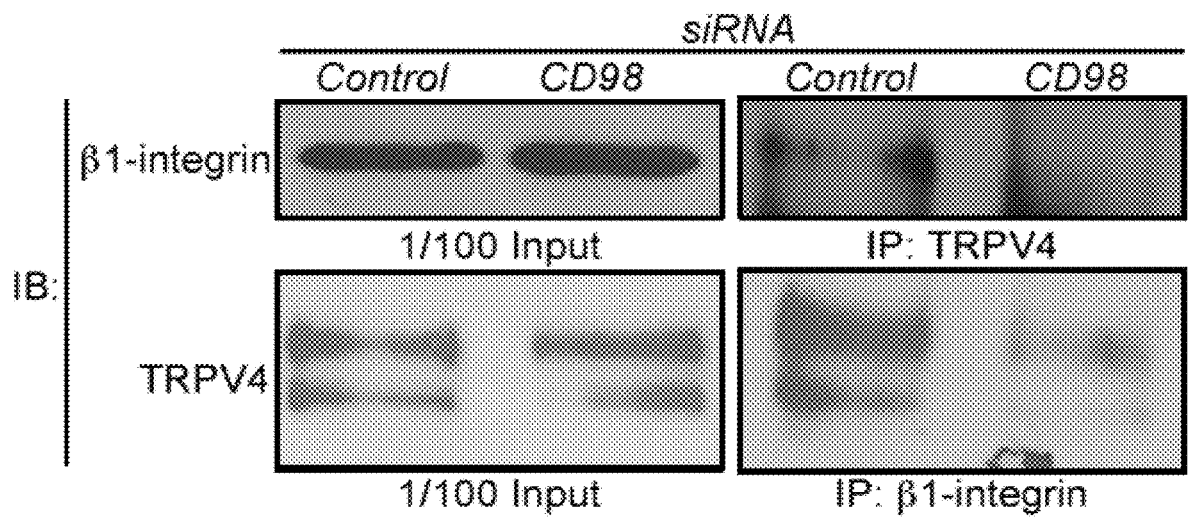
FIG. 3 demonstrates that CD98 mediates the binding between TRPV4 and β1-integrin. The cells were transfected with control or CD98 siRNA. The amount of each compo-nent in the total cell lysates is given in the left panel. In the right lanses the cell lysates were immunoprecipitates with rabbit anti-TRPV4 (upper) or mouse anti-β1-integrin anti-body (lower).

CD98 mediates the binding between TRPV4 and β1-integrin at focal adhesion. The question is what the molecular mechanism is by which CD98 mediates the signaling from β1-integrin to TRPV4. CD98 is important for surface expression and clustering of β1-integrin in MCF7 cells (11). Therefore, it was examined whether CD98 mediates the binding between β1-integrin and TRPV4 using siRNA-based knockdown of CD98. Transfection of HUVE cells with CD98 siRNA resulted in decreased association of TRPV4 and β1-integrin as well as loss of TRPV4 from focal adhesions that still retained integrin and vinculin (FIG. 3). In addition, when monolayer CD98 siRNA-treated HUVE cells are scratched and cultured, the scratch is normally restored by cell migration same as the cells treated with control siRNA (data not shown). Thus, CD98 deficiency doesn't affect the formation of focal adhesion.

Figure 4:
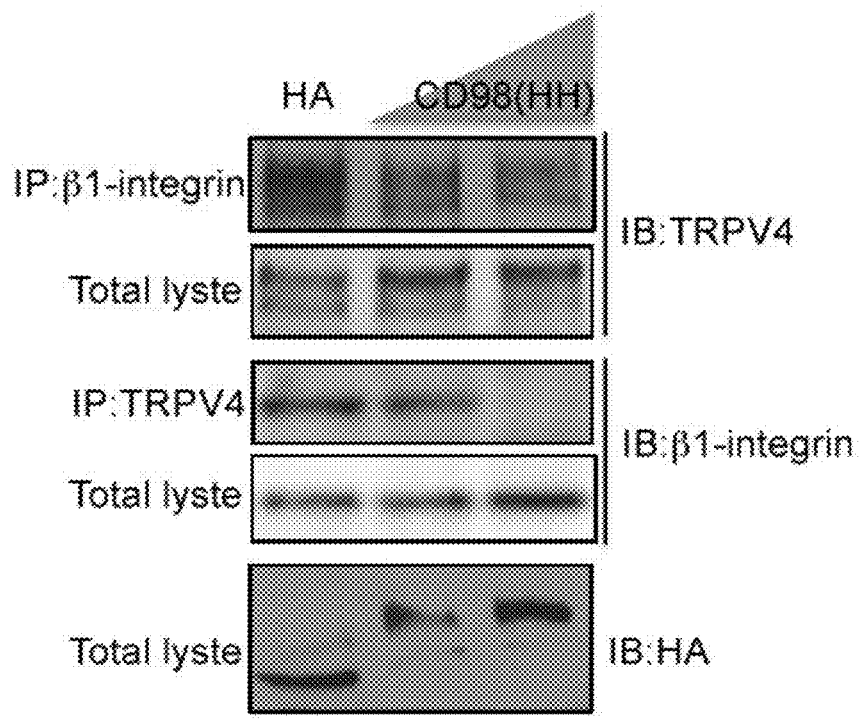
FIG. 4 demonstrates the effects of CD98 high homology domain on the binding between β1-integrin and TRPV4. 2.5, 5 μg HA-linked CD98 high homology domain or 5 μg HA vector was transfected into HEK293T cells, and the binding assay was performed 24 h later. The bottom panel gives the amount of each transgene in total cell lysates of respective transfectants. In the top or the 3rd panel, the lysates were immunoprecipitated with an anti-β1-integrin or TRPV4 anti-body, and the amount of TRPV4 or β1-integrin in the precipitates was blotted with each antibodies. The $2^{nd}$ or the $4^{th}$ panel gives the amount of β1-integrin or TRPV4 in total cell lysates.

As described above, high homology domain of CD98 is important for the binding to either β1-integrin or TRPV4. The effects of loss of only that region on β1-integrin-TRPV4 interaction were therefore examined. β1-integrin binding to TRPV4 was indeed inhibited by loss of the high homology domain (FIG. 4). Therefore, CD98 mediates the binding between β1-integrin and TRPV4 at focal adhesion through the high homology domain of CD98.

Figure 5:
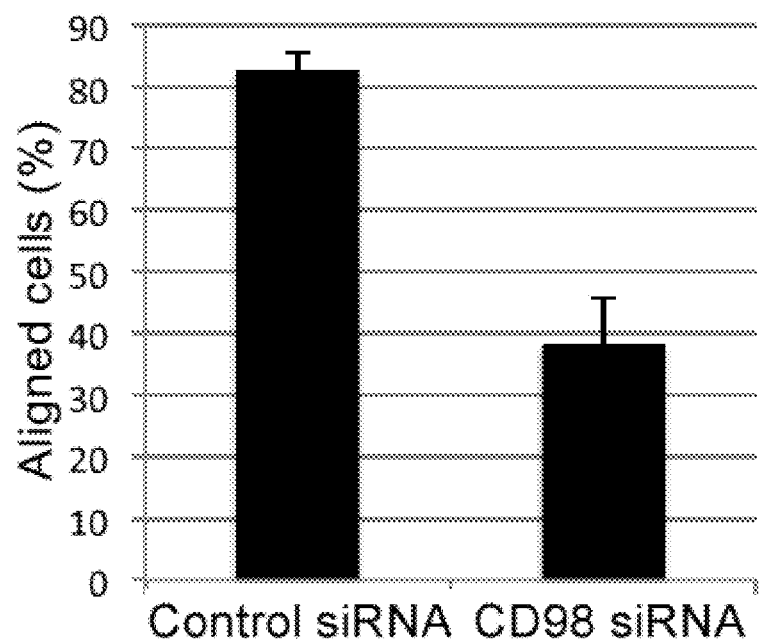
FIG. 5 demonstrates that CD98 involves actin rearrange-ment on mechanotransduction. The graph depicts the per-centage of cell oriented at 90±30 degrees (aligned) relative to the direction of applied strain in control and CD98 knockdown HUVE cells; error bars indicate SEM.

CD98 involves actin rearrangement on mechanotransduction. To confirm that CD98 translates the mechanical signal from β1-integrin to TRPV4 by mediating the binding, it was examined whether CD98 is required for the actin arrangement induced by cyclic strain. To analyze it, HUVE cells were cultured on flexible fibronectin-coated substrates and subjected to 20% uniaxial cyclic strain using a FlexrCell™ Tension Plus system. Fluorescence microscope analysis of cells labeled with Alexa 488-phalloidin combined with computerized morphometry revealed that stress fibers thickened in these cells, and most realigned perpendicular to the main axis of the applied strain with 2 hours after force application in control siRNA transfected HUVE cells. In contrast, this response was abolished by the treatment with CD98 siRNA (FIG. 5).

Figure 6A:
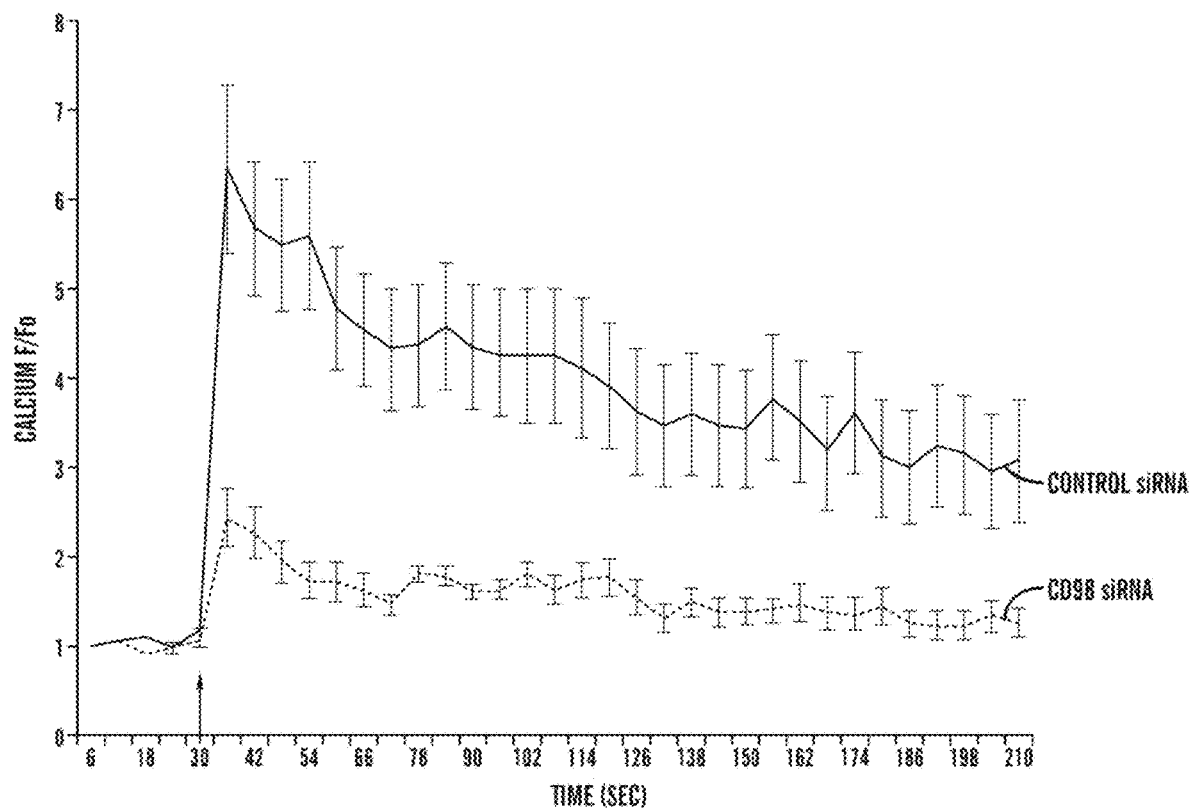
FIGS. 6A-6D demonstrate that CD98 is required for mechanical activation of TRPV4.
Figure 6B:
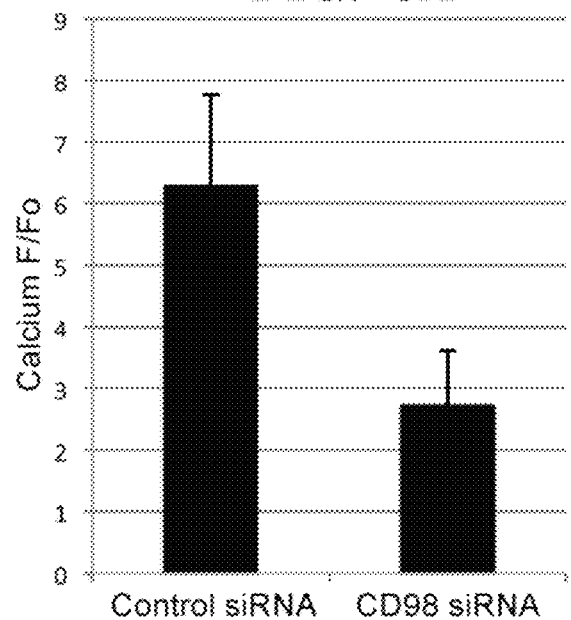
Figure 6C:
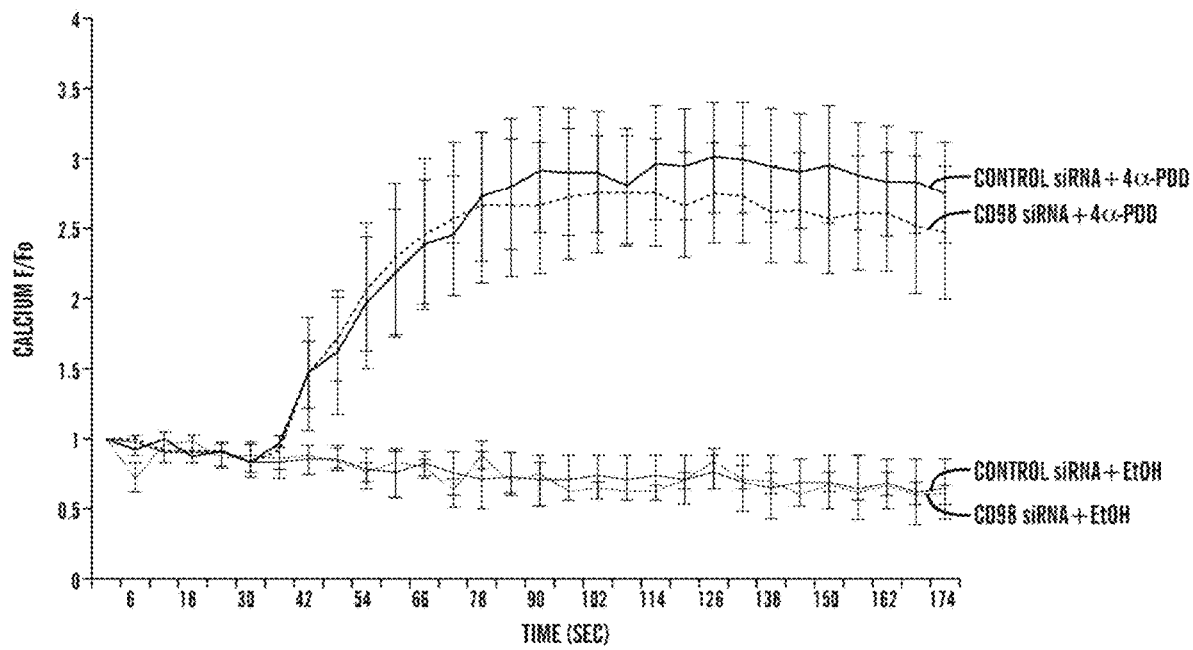
Figure 6D:
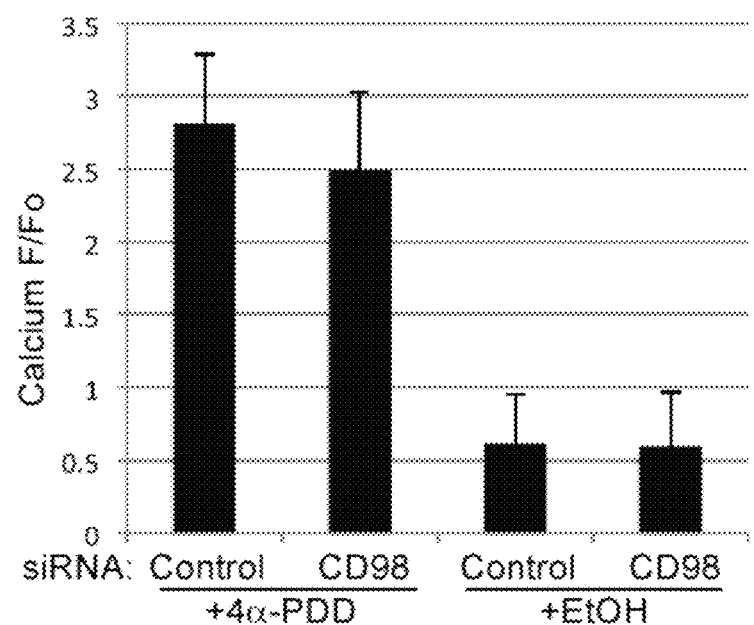
Figure 7:
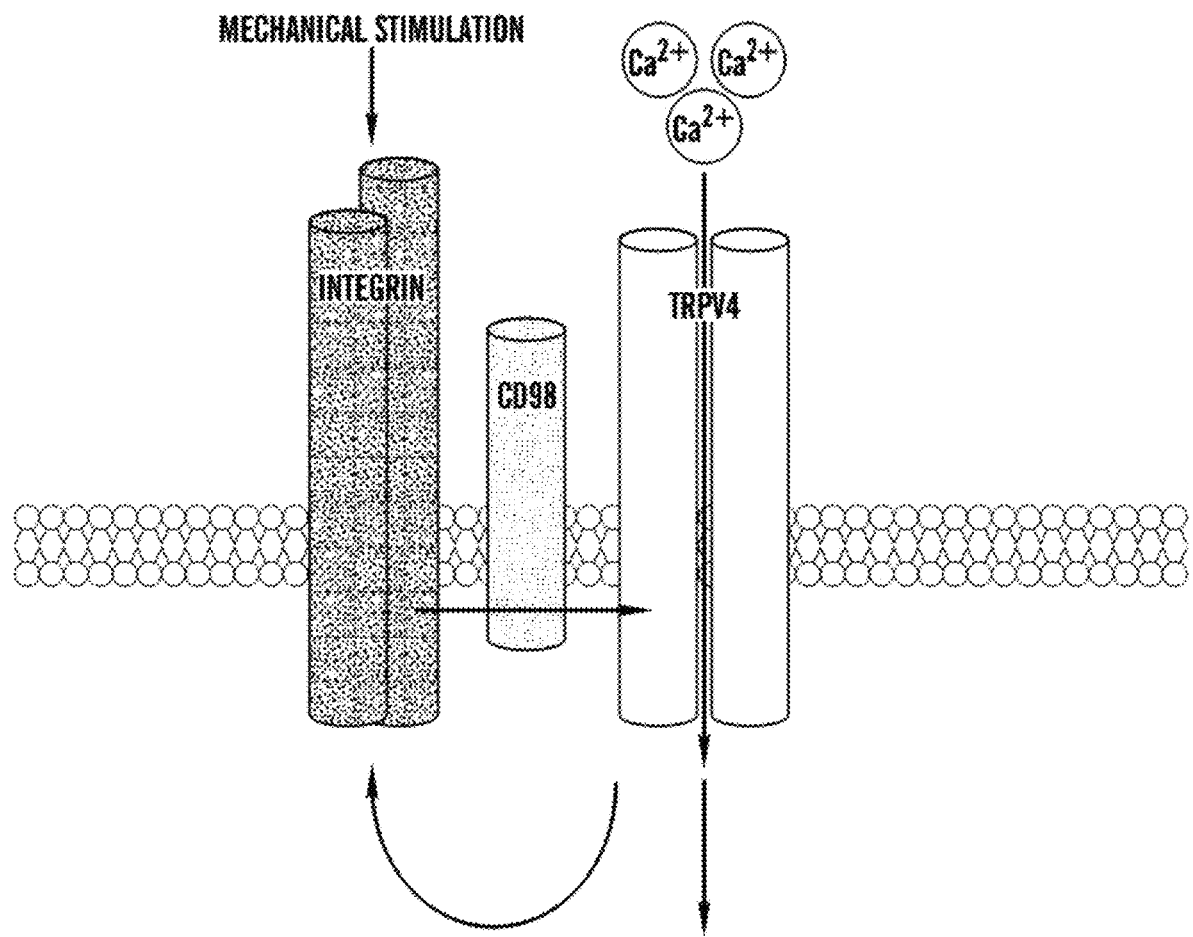
FIG. 7 depicts a schematic model of mechanotransduction through integrin-CD98-TRPV4 complex. This study pro-poses that integrin transduces mechanical cues to TRPV4 through CD98. TRPV4 induces calcium signaling by β1-in-tegrin and also activates integrin signaling.

Specific inhibition of mechanical activation of TRPV4 activity. Moreover, TRPV4 is specifically activated by mechanical strain (12). To examine whether CD98 transduces the signal by mechanical stimulation through TRPV4, the calcium influx by mechanical stimulation was investigated. Transient increases in intracellular calcium were detected quickly after force application in HUVE cells treated with control siRNA. However, HUVE cells treated with CD98 siRNA didn't show this response (FIG. 6A). TRPV4 is also activated by chemical stimulation such as 4α-phorbol 12, 13-didecanoate (4α-PDD). 4α-PDD produces a rapid increase in intracellular calcium in HUVE cells treated with either control or CD98 siRNA (FIG. 6B), indicating that formation of the CD98-TRPV4-B1-Integrin complex is required for mechanical activation of calcium influx through TRPV4, but not for TRPV4 activation by chemical stimuli.

Discussion

TRPV4 and β1-integrin are mechanosensors. The data presented herein indicate that e that CD98 mediates the binding of TRPV4 to β1-integrins, and that it is required for mechanical, but not chemical, activation of TRPV4. This study has revealed that the signaling pathways of TRPV4 activation are different between mechanical and chemical cues.

TRPV4 has been implicated in the development of pulmonary edema induced by various stimuli, including heart failure that acts by increasing pulmonary vascular pressure, as well as chemicals and inflammation. Importantly, in recent studies, pulmonary edema induced by IL2 was studied in a microengineered human "Lung-on-a-chip" microfluidic device containing an artificial alveolar-capillary interface lined by living human lung alveolar and capillary cells that experiences physiological breathing motions and regenerates a functional vascular permeability barrier in vitro (Huh D et al., 2010). Using this engineering approach, it was demonstrated that: a) IL2 produces clinical manifestations of pulmonary edema (vascular leakage, fibrin clot formation, and compromised oxygen transport) in vitro, b) physiological breathing motions enhance IL2-induced increases in pulmonary vascular leakage by ~4-fold, and c) a chemical inhibitor of TRPV4 activity (e.g. GSK2193874) can prevent pulmonary vascular leakage and lung edema development in a human lung-on-a-chip microdevice that effectively mimics lung microarchitecture and physiology of the human alveolar-capillary interface (Huh D et al., 2012). Importantly, another group also has shown that same TRPV4 inhibitor prevents cardiogenic pulmonary edema induced by increases pulmonary vascular pressure in rats, mice and dog (Thorneloe K S et al., 2012). These finding indicate that treatments targeting TRPV4 can permit new pulmonary edema therapies, and hence, understanding the molecular determinants responsible for mechanical signaling through TRPV4 has important clinical significance for treatment of pulmonary edema.

TRPV4 is also present on many cell types and in many tissues, and it can be activated by chemical (e.g., arachidonic acid metabolites epoxyeicosatrienoic acids 5,6-EET and 8,9-EET) as well as mechanical cues (e.g., breathing motions, ECM strain, fluid shear stress, pulmonary vascular pressure, barotrauma). TRPV4 is also involved in the regulation of diverse bodily functions including control serum osmolarity, nociception and thermal sensing and regulation in the central nervous system, bone formation and remodeling, bladder tone, motor and sensory neuritogenesis, as well as inflammation and energy homeostasis in adipocytes. Thus, the breadth of functions of this ubiquitous membrane ion channel would predict that systemic administration of inhibitors TRPV4 activity might lead to diverse adverse effects and severe systemic dose-limiting toxicities. Thus, the identification of sites within CD98 and TRPV4 that are responsible for their intermolecular binding interactions, as well as for mechanical activation of TRPV4 by physical forces applied to integrins, permits the use more specific and/or targeted inhibitors of pulmonary edema development.

Materials and Methods

Cell culture. Human Umbilical Vein Endothelial Cells (HUVE cells) and Human embryonic kidney 293T (HEK293T) cells were obtained from the culture collection organization AMERICAN TYPE CULTURE COLLECTION™ (ATCC). HUVE cells were cultured in supplemented endothelial growth medium (EGM-2; Lonza). HEK293T cells were cultured in Dulbecco's modified Eagle's medium (DMEM) supplemented with 10% fetal bovine serum (FBS) and 100 units/ml penicillin and 100 μg/ml streptomycin.

siRNA knock down of CD98. RNA interference assay was conducted with human CD98 siRNA duplexes: 5'-GAAUGGUCUGGUGAAGAUC-3' (SEQ ID NO: 21) and 5'-GAUCUUCACCAGACCAUUC-3' (SEQ ID NO: 22). Cells were transfected with 50 nM of the siRNA duplexes in Opti-MEM™ (Invitrogen) using silentFect Lipid Reagent for RNAi (BIO-RAD), according to the manufacturer's instructions.

Antibodies. Primary antibodies used for immunofluorescent staining, immunoprecipitation assay and immunoblotting included rabbit anti-rat TRPV4 antibody (Almone), mouse anti-human β1-integrin (BD Transduction Laboratories), rabbit anti-human CD98 antibody (abcam), mouse anti-chicken vinculin antibody (sigma) and Alexa fluor 488 phalloidin (Invitrogen).

Immunoprecipitation. Cells were extracted in ice-cold TRITON™ buffer (50 mM Tris-HCL, pH 7.4, containing 150 mM NaCl, 1% TRITONX100™, 5 mM EDTA). Cell extracts were centrifuged at 10000 g for 15 min at 4° C. prior to being immunoprecipitated with each antibodies and DYNABEADS™ Magnetic Beads (Invitrogen) at 4° C. Subsequently the beads were isolated by magnet and washed five times with TRITON™ buffer and then were detected by SDS-PAGE and immunoblotting.

Mechanical strain application, measurement of cell orientation, Calcium Imaging were performed as described (Thodeti et al., 2009)

References

TRPV4 channels mediate cyclic strain-induced endothelial cell reorientation through integrin-to-integrin signaling. Thodeti C K, Matthews B D, Ravi A, Mammoto A, Ghosh K, Bracha A L, Ingber DE. Circ Res. 2009 104:1123-1130.

Ultra-rapid activation of TRPV4 ion channels by mechanical forces applied to cell surface β1-integrins. Matthews B D, Thodeti C K, Tytell J D, Mammoto A, Overby D R, Ingber D E. Integr Biol. 2010 2:435-442

A human disease model of drug toxicity-induced pulmonary edema in a lung-on-a-chip microdevice. Huh D, Leslie D C, Matthews B D, Fraser J P, Jurek S, Hamilton G A, Thorneloe K S, McAlexander M A, Ingber D E. Sci Transl Med. 2012 4:159ra147

CD98 mediates mechanical signal from β1-integrin to TRPV4. Hirano-Kobayashi M, Matthews B D, Ingber D E. In preparation Example 2

CD98 Mediates Mechanical Signaling from β1-integrin to TRPV4 Channels in the Focal Adhesion Cellular mechanotransduction—the process by which cells convert physical forces applied on their surface into changes in intracellular biochemistry and gene expression—is fundamental to development, physiology and disease. One of the most rapid (<5 msec) mechanotransduction events in human cells involves integrin-dependent activation of the stress-sensitive membrane ion channel, TRPV4 (Transient receptor potential vanilloid 4). However, the molecular mechanism by which force applied to cell surface integrins triggers this "early-immediate" mechanical signaling response is unknown, and it remains unclear whether this pathway is distinct from chemical activation mechanisms used by the channel. It is described herein that physical forces applied to cell surface β1-integrins are transmitted to the integrin-associated transmembrane protein CD98 that, in turn, directly transfers force to associated TRPV4 membrane ion channels, which results in their activation. B1-integrin, TRPV4 and CD98 all co-localize in focal adhesions in living cells, and they co-associate within common immunoprecipitable protein complexes. Recruitment of TRPV4 can be prevented by suppressing CD98 expression with specific siRNA, and CD98 knock down also inhibits calcium influx through TRPV4 channels induced by mechanical forces, but not by chemical activators. The portions of the β1-integrin, CD98 and TRPV4 molecules that mediate these interactions also have been identified. Together, these findings demonstrate that CD98 mediates rapid, mechanical force-induced activation of TRPV4 by facilitating direct force transfer between β1-integrin and this ion channel within a common binding complex in the focal adhesion.

Cellular mechanotransduction is critical for control of the growth and development of all tissues, and deregulation of this process contributes to the development of numerous diseases (ref1). Force sensing is mediated by cell surface integrin receptors (ref2), which is thought to induce mechanochemical transduction by transmitting these stresses across the cell surface and inducing deformations in proteins, such as talin and vinculin (ref3), that form the cytoskeletal backbone of the focal adhesion. However, the finding that forces application to β1-integrins results in almost immediate (<5 millisec) activation of calcium influx through TRPV4 membrane ion channels in endothelial cells (ref4) raises the possibility that ultra-rapid mechanochemical conversion is mediated by direct mechanical signal transfer from integrins to TRPV4 channels. Understanding this mechanism is important because mechanical activation of TRPV4 channels in endothelial cells has been shown to play a central role in the development of pulmonary edema, and TRPV4 antagonists can effectively suppress development of these disease (ref5, 6). Thus, described herein is the exploration of how mechanical forces applied to integrins activate TRPV4 channels on the endothelial cell surface.

Figures 8A, 8B:
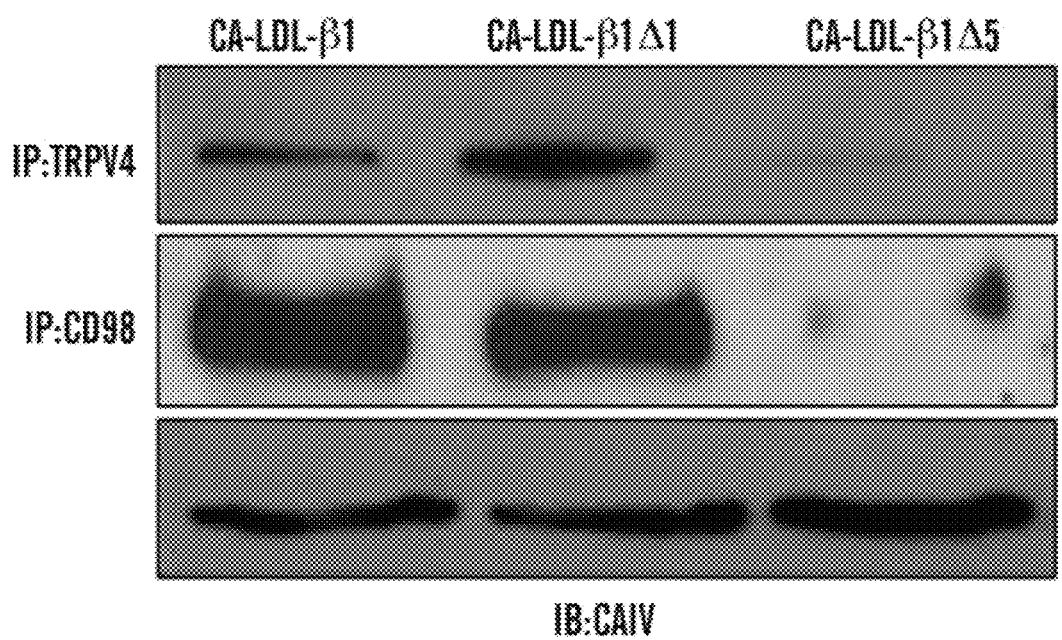
FIG. 8A depicts a diagram of genetically engineered mutant β1-integrin DNA construct consisting of the carbonic anhydrase IV (CAIV) enzyme extracellular domain (EC) connected to the transmembrane (TM) domain of LDL, and the β1-integrin intracellular (IC) domain.
FIG. 8B depicts immunoblot results demonstrating CD98 and TRPV4 bind the same region of β1-integrin. β1 construct has full-length intracellular region of β1-integrin. β1Δ1 and β1Δ5 are sequential deletion constructs and β1Δ1 was replaced the region next to TM domain with alanines. β1 or β1Δ1 β1Δ5 was transfected into HEK293T cells 12 h after plating, and the cells were harvested 24 h later. The bottom panel gives the Western blotting for the expression of each transgene in total cell lysates of respective transfectants. In the upper and middle panels, the lysates were immunoprecipitated with the anti TRPV4 or CD98 antibody and the presence or absence of each molecule in the immunoprecipitates was blotted with anti CAIV antibody.
Figure 10:
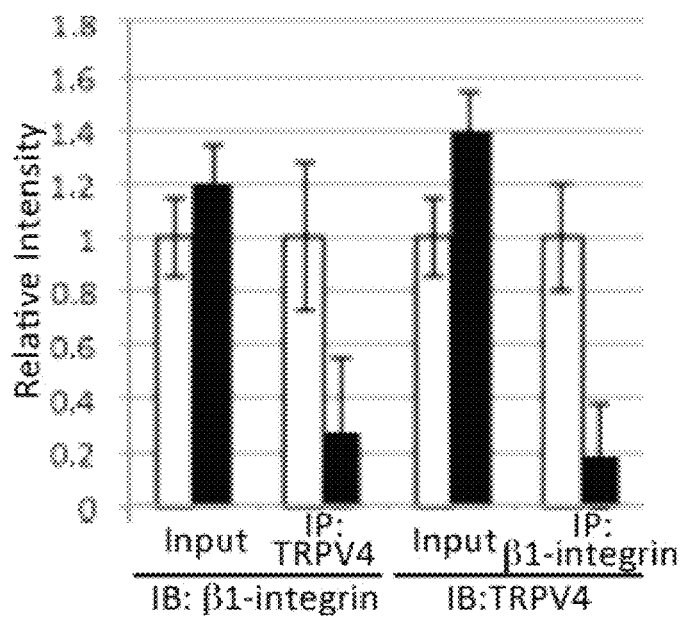
FIG. 10 demonstrates that CD98 mediates the binding between TRPV4 and β1-integrin. The quantification effects of the experiment depicted in FIG. 3 from n=3 was carried out using ImageJ™ software.
Figure 11:
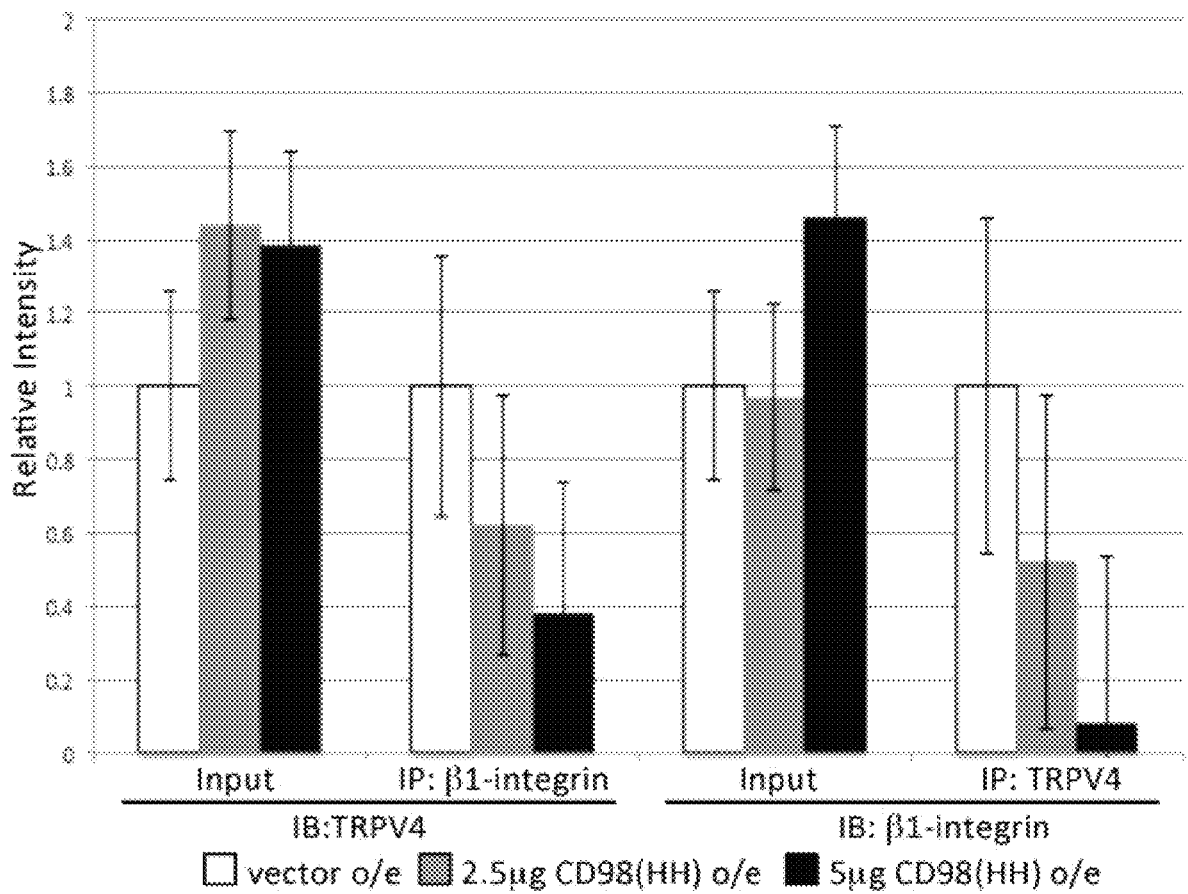
FIG. 11 demonstrates the effects of CD98 high homology domain on the binding between β1-integrin and TRPV4. The quantification of the experimental results depicted in FIG. 4 from n=3 was carried out using ImageJ™ software.

It was first examined whether the transmembrane amino acid transporter CD98 mediates force transfer between β1-integrin and TRPV4. When HEK293T cells were transfected with β1-integrin mutant constructs and immunoprecipitation assays performed, it was confirmed that CD98 specifically binds to the β1-integrin tail region (FIG. 8B). Interesting, using the same approach, it was found that TRPV4 also interacts with the same region of β1-integrin molecule (FIG. 8B). In separate studies with human umbilical vein endothelial (HUVE) cells, it was found that CD98 and β1-integrin can be co-precipitated using anti-TRPV4 antibody (FIG. 1A), and that TRPV4 can be similarly precipitated using either anti-β1-integrin or anti-CD98 antibodies (FIG. 1B). Moreover, TRPV4 colocalizes with both CD98 and vinculin within spontaneously formed focal adhesions, when analyzed by total internal reflection fluorescence (TIRF) microscopy (data not shown). These findings indicated that β1-integrin, CD98 and TRPV4 co-associate with each other and with cytoskeletal proteins within focal adhesions.

To explore in greater detail how TRPV4 senses mechanical signals, the transmembrane and C-terminal regions of TRPV4 were genetically deleted; however, this did not alter its ability to bind to either β1-integrin or CD98 when analyzed using the immunoprecipitation assay (FIGS. 2A-2D). Similarly, when the proline rich domain of TRPV4 was deleted, it also had no effect on its ability to associate with these two molecules (FIG. 2B). However, deletion of the three ankyrin repeat domains (237-266aa, 284-313aa, and 369-398aa) in the N-terminus of TRPV4, was sufficient to completely inhibit binding to both β1-integrin and CD98 (FIG. 2B).

Thus, the findings suggest that the ankyrin repeat regions of TRPV4 mediate formation of the integrin-CD98-TRPV4 complex; however, it does not clarify how CD98 is recruited to this complex. CD98 is also a membrane protein composed of an N-terminal cytoplasmic domain, an intervening transmembrane domain, and C-terminal extracellular domain. Deletion of the C-terminal region of CD98 did not alter its ability to bind to either β1-integrin or TRPV4 (FIG. 2D). In contrast, deletion of a 50 amino acid (160-210aa) high homology domain within the CD98 N-terminus that is highly conserved from drosophila to mammals completely blocked its ability to associate with either β1-integrin or TRPV4 (FIG. 9). Thus, β1-integrin, CD98 and TRPV4 co-associate through binding interactions between the last 6aa residues on the integrin cytoplasm tail, the high homology domain of CD98 and the ankyrin repeat domains of TRPV4.

It was next asked whether CD98 serves to link β1-integrin to TRPV4. Knock down of CD98 expression in HUVE cells using siRNA greatly reduced the amount of both CD98 and TRPV4 within focal adhesions, although it had no effect on recruitment of either integrins or vinculin (data not shown) to these anchoring complexes, and it did not interfere with cell migration in scratch wound assays (data not shown). Thus, CD98 is not required for focal adhesion formation or function. However knock down of CD98 expression in HUVE cells using siRNA greatly reduced the amount of the binding between β1-integrin and TRPV4 (FIG. 3). Although TRPV4 expression was not decreased, TRPV4 couldn't localize at focal adhesions (data not shown).

Figure 12:
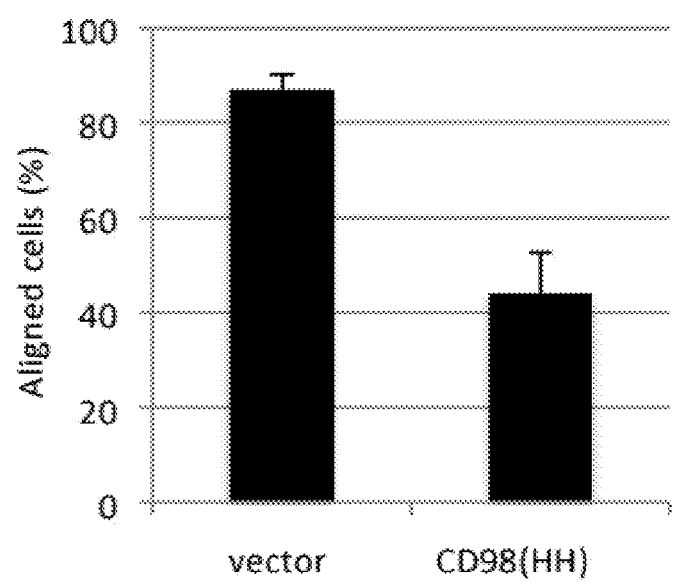
FIG. 12 depicts a graph of the percentage of cells oriented 90±30 degrees (aligned) relative to the direction of the applied strain in vector or CD98(HH) overexpressing HUVE cells; error bars indicate SEM.

As described above, high homology domain of CD98 is important for the binging to either β1-integrin or TRPV4. It was next examined if the high homology domain of CD98 shows dominant negative effect by immunoprecipitation assay and stretching assay. β1-integrin binding to TRPV4 was decreased by overexpressing high homology domain of CD98 (FIG. 4). And the cells overexpressing high homology domain of CD98 didn't show actin rearrangements after giving mechanical strain (FIG. 12). These data indicate that the high homology domain of CD98 can compete with endogenous CD98 on mediating the binding between TRPV4 and β1-integrin. Therefore, CD98 mediates the binding between β1-integrin and TRPV4 at focal adhesion through high homology domain of CD98.

CD98 involves actin rearrangement on mechanotransduction

To confirm that CD98 translates the mechanical signal from β1-integrin to TRPV4 by mediating the binding, it was examined whether CD98 is required for the actin arrangement induced by cyclic strain. To analyze it, HUVE cells were cultured on flexible fibronectin-coated substrates and subjected to 20% uniaxial cyclic strain using a FlexrCell Tension Plus™ system. Fluorescence microscope analysis of cells labeled with Alexa 488-phalloidin combined with computerized morphology revealed that stress fibers thickened in these cells, and most realigned perpendicular to the main axis of the applied strain with 2 hours after force application in control siRNA transfected HUVE cells. In contrast, this response was abolished by the treatment with CD98 siRNA (FIG. 5).

Moreover, TRPV4 is specifically activated by mechanical strain (ref10). To examine whether CD98 transduce the signal by mechanical stimulation through TRPV4, the calcium influx by mechanical stimulation was examined. Transient increases in intracellular calcium were detected quickly after force application in HUVE cells treated with control siRNA. However, HUVE cells treated with CD98 siRNA didn't show this response (FIG. 6A). TRPV4 is also activated by chemical stimulation such as 4a-phorbol 12, 13-didecanoate (4a-PDD). 4a-PDD produces a rapid increase in intracellular calcium in HUVE cells treated with either control or CD98 siRNA (FIG. 6B), indicating that CD98 plays a role in the calcium influx through the activation of TRPV4 by mechanical, but not chemical.

TRPV4 and β1-integrin are mechanosensors.

The molecular mechanism between mechanosensors is still unclear. It is proposed herein that CD98 mediates the binding of TRPV4 to β1-integrins, and that it is required for mechanical, but not chemical, activation of TRPV4. This study has revealed that the signaling pathway of TRPV4 activation is different between mechanical and chemical cue.

Surprisingly, CD98 mediated only mechanical cues from β1-integrin to TRPV4. Although the localization of TRPV4 at focal adhesion was decreased in CD98 knockdown cells, TRPV4 localization was visible at the cell membrane by TIRF. These data indicate that CD98 mediates TRPV4 to localize at focal adhesion and transfers mechanical cues from β1-integrin.

TRPV4 is phosphorylated when it is activated (ref8). The cytoplasmic region of β1-integrin interacts with many kinases such as FAK, ILK and Src. Without wishing to be limited by theory, it is contemplated herein that a certain kinase, which is included in integrin complex, phosphorylates TRPV4 in response to mechanical cues.

TRPV4 has been implicated in the development of pulmonary edema induced by various stimuli, including heart failure that acts by increasing pulmonary vascular pressure, as well as chemicals and inflammation. Importantly, pulmonary edema induced by IL2 has been studied in a microengineered human "Lung-on-a-chip" microfluidic device containing an artificial alveolar-capillary interface lined by living human lung alveolar and capillary cells that experiences physiological breathing motions and regenerates a functional vascular permeability barrier in vitro (ref9). Using this engineering approach, it was demonstrated that: a) IL2 produces clinical manifestations of pulmonary edema (vascular leakage, fibrin clot formation, and compromised oxygen transport) in vitro, b) physiological breathing motions enhance IL2-induced increases in pulmonary vascular leakage by ~4-fold, and c) a chemical inhibitor of TRPV4 activity (GSK2193874) can prevent pulmonary vascular leakage and lung edema development in a human lung-on-a-chip microdevice that effectively mimics lung microarchitecture and physiology of the human alveolar-capillary interface (ref11). That same TRPV4 inhibitor prevents cardiogenic pulmonary edema induced by increasing pulmonary vascular pressure in rats, mice and dog (ref12).

Thus, TRPV4 can be a novel target for new pulmonary edema therapies, and hence, understanding the molecular determinants responsible for mechanical signaling through TRPV4 can have important clinical significance for treatment of pulmonary edema. But TRPV4 is also present on many cell types and in many tissues, and it can be activated by chemical (e.g., arachidonic acid metabolites epoxyeicosatrienoic acids 5,6-EET and 8,9-EET) as well as mechanical cues (e.g., breathing motions, ECM strain, fluid shear stress, pulmonary vascular pressure, barotrauma). TRPV4 is also involved in the regulation of diverse bodily functions including control serum osmolality, nociception and thermal sensing and regulation in the central nervous system, bone formation and remodeling, bladder tone, motor and sensory neuritogenesis, as well as inflammation and energy homeostasis in adipocytes (ref18-37). Thus, the breadth of functions of this ubiquitous membrane ion channel predict that systemic administration of inhibitors of TRPV4 activity can lead to diverse adverse effects and severe systemic dose-limiting toxicities. Thus, the identification of sites within CD98 and TRPV4 that are responsible for their intermolecular binding interactions, as well as for mechanical activation of TRPV4 by physical forces applied to integrins, can lead to the development of new and improved inhibitors of pulmonary edema development. Described herein are methods and compositions that permit specific inhibition of TRPV4 activation due to mechanical cues.

Methods

Methods were as detailed in Example 1

REFERENCES

1. Ingber D E. Mechanobiology and diseases of mechanotransduction. Ann Med 2003; 35:564-77.
2. Wang N, Butler J P and Ingber D E. Mechanotransduction across the cell surface and through the cytoskeleton. Science 1993
3. Wirtz H R, Dobbs L G. The effects of mechanical forces on lung functions. Respir Physiol. 2000; 119:1-17.
4. Matthews B D, Thodeti C K, Tytell J D, Mammoto A, Overby D R, Ingber D E. Ultra-rapid activation of TRPV4 ion channels by mechanical forces applied to cell surface beta1 integrins. Integr Biol (Camb) 2010; 2:435-42.
5. Thorneloe K S, Cheung M, Bao W, et al. An orally active TRPV4 channel blocker prevents and resolves pulmonary edema induced by heart failure. Sci Transl Med 2012; 4:159ra48.
6. Huh D, Leslie D C, Matthews B D, et al. A human disease model of drug toxicity-induced pulmonary edema in a lung-on-a-chip microdevice. Sci Transl Med 2012; 4:159ra47.
7. Thodeti C K, Matthews B, Ravi A, et al. TRPV4 channels mediate cyclic strain-induced endothelial cell reorientation through integrin-to-integrin signaling. Circ Res 2009; 104:1123-30.
8. Kolesnikova T V, Mannion B A, Berditchevski F, Hemler M E. Beta1 integrins show specific association with CD98 protein in low density membranes. BMC Biochem 2001; 2:10

9. Feral C C, Zijlstra A, Tkachenko E, Prager G, Gardel M L, Slepak M, Ginsberg M H. CD98 hc (SLC3A2) participates in fibronectin matrix assembly by mediating integrin signaling. J Cell Biol. 2007; 178:701-11.
10. Mammoto A, Mammoto T, Ingber D E. Mechanosensitive mechanisms in transcriptional regulation. J Cell Sci 2012; 125:3061-73.
11. Cai S, Bulus N, Fonseca-Siesser P M, Chen D, Hanks S K, Pozzi A, Zent R. CD98 modulates integrin beta1 function in polarized epithelial cells. J Cell Sci. 2005; 118:889-99.
12. Adapala R K, Talasila P K, Bratz I N, Zhang D X, Suzuki M, Meszaros J G, Thodeti C K. PKCα mediates acetylcholine-induced activation of TRPV4-dependent calcium influx in endothelial cells. Am J Physiol Heart Circ Physiol 2011; 301:H757-65.
13. Thorneloe K S, Cheung M, Bao W, et al. An Orally Active TRPV4 Channel Blocker Prevents and Resolves Pulmonary Edema Induced by Heart Failure. Sci Transl Med 2012; 4:159ra148
14. Liedtke W. TRPV4 as osmosensor: a transgenic approach. Pflugers Arch 2005; 451:176-80.
15. Liedtke W, Friedman J M. Abnormal osmotic regulation in trpv4-/- mice. Proc Natl Acad Sci USA 2003; 100: 13698-703.
16. Strotmann R, Harteneck C, Nunnenmacher K, Schultz G, Plant T D. OTRPC4, a nonselective cation channel that confers sensitivity to extracellular osmolarity. Nat Cell Biol 2000; 2:695-702.
17. Liedtke W, Choe Y, Marti-Renom M A, et al. Vanilloid receptor-related osmotically activated channel (VR-OAC), a candidate vertebrate osmoreceptor. Cell 2000; 103:525-35.
18. Mizuno A, Matsumoto N, Imai M, Suzuki M. Impaired osmotic sensation in mice lacking TRPV4. Am J Physiol Cell Physiol 2003; 285:C96-101.
19. Jin M, Berrout J, Chen L, O'Neil R G. Hypotonicity-induced TRPV4 function in renal collecting duct cells: modulation by progressive cross-talk with Ca2+-activated K+ channels. Cell calcium 2012; 51:131-9.
20. Chen L, Liu C, Liu L. Osmolality-induced tuning of action potentials in trigeminal ganglion neurons. Neuroscience letters 2009; 452:79-83.
21. Li J, Wang M H, Wang L, et al. Role of transient receptor potential vanilloid 4 in the effect of osmotic pressure on myocardial contractility in rat. Sheng li xue bao: [Acta physiologica Sinica] 2008; 60:181-8.
22. Zhang Y, Wang Y H, Ge H Y, Arendt-Nielsen L, Wang R, Yue S W. A transient receptor potential vanilloid 4 contributes to mechanical allodynia following chronic compression of dorsal root ganglion in rats. Neuroscience letters 2008; 432:222-7.
23. Alessandri-Haber N, Yeh J J, Boyd A E, et al. Hypotonicity induces TRPV4-mediated nociception in rat. Neuron 2003; 39:497-511.
24. Bang S, Yang T J, Yoo S, Heo T H, Hwang S W. Inhibition of sensory neuronal TRPs contributes to antinociception by butamben. Neuroscience letters 2012; 506:297-302.
25. Liu T T, Bi H S, Lv S Y, Wang X R, Yue S W. Inhibition of the expression and function of TRPV4 by RNA interference in dorsal root ganglion. Neurological research 2010; 32:466-71.
26. Guler A D, Lee H, Iida T, Shimizu I, Tominaga M, Caterina M. Heat-evoked activation of the ion channel, TRPV4. J Neurosci 2002; 22:6408-14.
27. Chung M K, Lee H, Caterina M J. Warm temperatures activate TRPV4 in mouse 308 keratinocytes. J Biol Chem 2003; 278:32037-46.
28. Mizoguchi F, Mizuno A, Hayata T, et al. Transient receptor potential vanilloid 4 deficiency suppresses unloading-induced bone loss. Journal of cellular physiology 2008; 216:47-53.
29. Rock M J, Prenen J, Funari V A, et al. Gain-of-function mutations in TRPV4 cause autosomal dominant brachyolmia. Nat Genet 2008; 40:999-1003.
30. Krakow D, Vriens J, Camacho N, et al. Mutations in the gene encoding the calcium-permeable ion channel TRPV4 produce spondylometaphyseal dysplasia, Kozlowski type and metatropic dysplasia. American journal of human genetics 2009; 84:307-15.
31. Birder L, Kullmann F A, Lee H, et al. Activation of urothelial transient receptor potential vanilloid 4 by 4alpha-phorbol 12,13-didecanoate contributes to altered bladder reflexes in the rat. J Pharmacol Exp Ther 2007; 323:227-35.
32. Gevaert T, Vriens J, Segal A, et al. Deletion of the transient receptor potential cation channel TRPV4 impairs murine bladder voiding. J Clin Invest 2007; 117:3453-62.
33. Thorneloe K S, Sulpizio A C, Lin Z, et al. N-((1S)-1-{[4-((2S)-2-{[(2,4-dichlorophenyl)sulfonyl]amino}-3-hydroxypropanoyl)-1-piperazinyl]carbonyl}-3-methylbutyl)-1-benzothiophene-2-carboxamide (GSK1016790A), a novel and potent transient receptor potential vanilloid 4 channel agonist induces urinary bladder contraction and hyperactivity: Part I. J Pharmacol Exp Ther 2008; 326:432-42.
34. Xu X, Gordon E, Lin Z, Lozinskaya I M, Chen Y, Thorneloe K S. Functional TRPV4 channels and an absence of capsaicin-evoked currents in freshly-isolated, guinea-pig urothelial cells Channels (Austin) 2009; 3:156-60.
35. Jang Y, Jung J, Kim H, et al. Axonal neuropathy-associated TRPV4 regulates neurotrophic factor-derived axonal growth. J Biol Chem 2012; 287:6014-24.
36. Ye L, Kleiner S, Wu J, et al. TRPV4 Is a Regulator of Adipose Oxidative Metabolism, Inflammation, and Energy Homeostasis. Cell 2012; 151:96-110.
37. Roca-Cusachs P, Iskratsch T, Sheetz M P. Finding the weakest link—exploring integrin-mediated mechanical molecular pathways. J Cell Sci 2012; 125:3025-38.
38. Thodeti C K, Matthews B, Ravi A, et al. TRPV4 channels mediate cyclic strain-induced endothelial cell reorientation through integrin-to-integrin signaling. Circ Res 2009; 104:1123-30.

What is claimed herein is:

1. A method of inhibiting mechanically-dependent activation of Transient Receptor Potential Vanilloid 4 (TRPV4), the method comprising contacting a mammalian cell with a nucleic acid encoding a polypeptide:
   - comprising a sequence with at least 95% identity to the sequence of SEQ ID NO: 1;
   - comprising no more than 200 amino acids; and
   - capable of inhibiting binding of TRPV4 or integrin to Cluster of Differentiation 98 (CD98).

2. The method of claim 1, wherein the polypeptide comprises the sequence of SEQ ID NO: 1.

3. The method of claim 1, wherein the polypeptide comprising a sequence with at least 95% identity to the sequence of SEQ ID NO: 1 comprises no more than 100 amino acids.

4. The method of claim 1, wherein the nucleic acid is a cDNA.

5. The method of claim 1, wherein the nucleic acid is in a vector.

6. The method of claim 1, wherein the nucleic acid is in a viral vector.

7. The method of claim 6, wherein the vector is an adeno-associated virus (AAV) vector.

8. The method of claim 1, wherein the nucleic acid is caused to penetrate a cell via electroporation or magnetoporation.

* * * * *